US008283356B2

(12) United States Patent
Baenteli et al.

(10) Patent No.: US 8,283,356 B2
(45) Date of Patent: *Oct. 9, 2012

(54) 2,4- DI(HETERO)-ARYLAMINO-PYRIMIDINE DERIVATIVES AS ZAP-70 AND/OR SYK INHIBITORS

(75) Inventors: Rolf Baenteli, Basel (CH); Marie Claude Bernhard, Basel (CH); Peter Buehlmayer, Basel (CH); Nigel Graham Cooke, Basel (CH); Rudolf Duthaler, Basel (CH); Klaus Hinterding, Basel (CH); Gebhard Thoma, Basel (CH); Maurice Van Eis, Basel (CH); Anette Von Matt, Basel (CH); Louis Walliser, Basel (CH); Gerhard Zenke, Basel (CH)

(73) Assignee: Novartis AG, Basel (CH)

( * ) Notice: Subject to any disclaimer, the term of this patent is extended or adjusted under 35 U.S.C. 154(b) by 227 days.

This patent is subject to a terminal disclaimer.

(21) Appl. No.: 12/686,863

(22) Filed: Jan. 13, 2010

(65) Prior Publication Data
US 2010/0152182 A1    Jun. 17, 2010

Related U.S. Application Data

(63) Continuation of application No. 11/377,716, filed on Mar. 16, 2006, now Pat. No. 7,671,063, which is a continuation-in-part of application No. PCT/EP2004/010348, filed on Sep. 15, 2004.

(30) Foreign Application Priority Data

Sep. 16, 2003  (GB) .................................. 0321710.6
Jun. 28, 2004  (GB) .................................. 0414440.8

(51) Int. Cl.
C07D 405/12    (2006.01)
C07D 239/48    (2006.01)
C07D 413/14    (2006.01)
A61K 31/506    (2006.01)

(52) U.S. Cl. ........................................ 514/275; 544/323
(58) Field of Classification Search .................. 544/323; 514/275
See application file for complete search history.

(56) References Cited

U.S. PATENT DOCUMENTS

| 5,958,935 | A | 9/1999 | Davis et al. |
| 6,093,716 | A | 7/2000 | Davis et al. |
| 6,114,333 | A | 9/2000 | Davis et al. |
| 6,235,746 | B1 | 5/2001 | Davis et al. |
| 6,593,326 | B1 | 7/2003 | Bradbury et al. |
| 7,671,063 | B2 * | 3/2010 | Baenteli et al. ............... 514/275 |
| 7,943,627 | B2 * | 5/2011 | Baenteli et al. ............... 514/275 |

FOREIGN PATENT DOCUMENTS

| WO | 97/19065 A1 | 5/1997 |
| WO | 98/41512 A1 | 9/1998 |
| WO | 00/12485 A1 | 3/2000 |
| WO | 00/39101 A1 | 7/2000 |
| WO | 01/25220 A1 | 4/2001 |
| WO | 01/60816 A1 | 8/2001 |
| WO | 01/64655 A1 | 9/2001 |
| WO | 01/64656 A1 | 9/2001 |
| WO | 02/056888 A2 | 7/2002 |
| WO | 03/018021 A1 | 3/2003 |
| WO | 03/030909 A1 | 4/2003 |
| WO | 03/063794 A2 | 8/2003 |
| WO | 03/078404 A1 | 9/2003 |
| WO | 2004/056786 A2 | 7/2004 |
| WO | 2004/074244 A2 | 9/2004 |
| WO | 2004/080980 A1 | 9/2004 |
| WO | 2005/026130 A1 | 3/2005 |
| WO | 2006/068770 A1 | 6/2006 |

OTHER PUBLICATIONS

Gura, Systems for identifying New Drugs are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10):1424-1431.*
Ghosh, et al., "2,4-BIS(Arylamino)-5-methylpyrimidines as Antimicrobial Agents", Journal of Medicinal Chemistry, vol. 10, N°5, p. 974 (1967).
Ghoneim, et al., "Synthesis and Evaluation of some 2-, 4- and 2,4-Di-substituted-6-methylpyrimidine Derivatives for Antimicrobial Activity", Journal of the Indian chemical society, Calcutta, vol. 63, N°10, pp. 914-917, 1986.
Ghosh, et al., "2,4-Bis(Arylamino)-6-Methyl Pyrimidines as Antimicrobial Agents", Journal of the Indian chemical society, Calcutta, vol. 58, N°5, pp. 512-513, 1981.
Traxler, "Protein tyrosine kinase inhibitors in cancer treatment", Expert Opinion on Therapeutic Patents, vol. 7 N°6, pp. 571-588, 1987. J.V. Simone, Introduction, Cecil Textbook of Medicine, 20th Edition, vol. 1 pp. 1004-1010, 1996.
Basford, et al., CAPLUS Abstract 41:763 (1947).
Coopman, et al., "The SYK tyrosine kinase suppresses malignant growth of human breast cancer cells", Nature vol. 406, pp. 742-747, Aug. 2000.

* cited by examiner

*Primary Examiner* — Deepak Rao
(74) *Attorney, Agent, or Firm* — Paul D. Strain, Esq.; Strain & Strain PLLC

(57) ABSTRACT

Disclosed are pyrimidine derivatives of formula

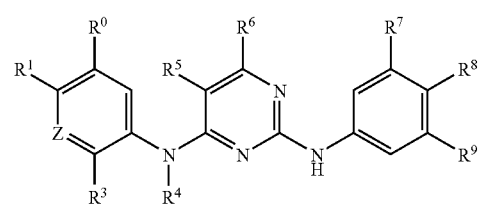

wherein $R^0$, $R^1$, $R^3$ to $R^9$, and Z have a signification as indicated in claim 1, which have interesting pharmaceutical properties.

11 Claims, No Drawings

2,4- DI(HETERO)-ARYLAMINO-PYRIMIDINE DERIVATIVES AS ZAP-70 AND/OR SYK INHIBITORS

This application is a U.S. Continuation of U.S. application Ser. No. 11/377,716 filed on Mar. 16, 2006, which was a national Phase filing of International Application No. PCT/EP04/10348 filed Sep. 15, 2004, and claims priority to GB application Serial No. 0321710.6 filed Sep. 16, 2003 and to GB application Serial number 0414440.8 filed on Jun. 28, 2004, the contents of which are incorporated herein by reference in their entirety.

The present invention relates to pyrimidine derivatives, to processes for their production, their use as pharmaceuticals and to pharmaceutical compositions comprising them.

More particularly the present invention provides in a first aspect, a compound of formula I wherein
Z is $=CR^2$— or $=N$—;
each of $R^0$, $R^1$, $R^2$, $R^3$ and $R^4$ independently is hydrogen; hydroxy; $C_1$-$C_8$alkyl; $C_2$-$C_8$alkenyl; $C_3$-$C_8$cycloalkyl; $C_3$-$C_8$cycloalkyl-$C_1$-$C_8$alkyl; hydroxy$C_1$-$C_8$alkyl; $C_1$-$C_8$alkoxy$C_1$-$C_8$alkyl; hydroxy$C_1$-$C_8$alkoxy$C_1$-$C_8$alkyl; aryl$C_1$-$C_8$alkyl which optionally may be substituted on the ring by hydroxy, $C_1$-$C_8$alkoxy, carboxy or $C_1$-$C_8$alkoxycarbonyl;
or $R^3$ and $R^4$ form together with the nitrogen and carbon atoms to which they are attached a 5 to 10 membered heterocyclic ring and comprising additionally 1, 2 or 3 heteroatoms selected from N, O and S;
or each of $R^1$, $R^2$ and $R^3$, independently, is halogen; halo-$C_1$-$C_8$alkyl; $C_1$-$C_8$alkoxy; $C_{2-8}$alkenyl-oxy; $C_{2-8}$alkynyl-oxy; halo-$C_1$-$C_8$-alkoxy; cyano-$C_1$-$C_8$-alkoxy; hydroxy$C_1$-$C_8$alkoxy; $C_1$-$C_8$alkoxy$C_1$-$C_8$alkoxy; $C_1$-$C_8$alkoxy$C_1$-$C_8$alkoxy$C_1$-$C_8$alkoxy; aryl; aryl$C_1$-$C_8$alkoxy; heteroaryl; heteroaryl-$C_1$-$C_4$alkyl; 5 to 10 membered heterocyclic ring; nitro; carboxy; $C_2$-$C_8$alkoxycarbonyl; $C_2$-$C_8$alkylcarbonyl; —N($C_1$-$C_8$-alkyl)C(O)$C_1$-$C_8$alkyl; —N($R^{10}$)$R^{11}$; —CON($R^{10}$)$R^{11}$; —SO$_2$N($R^{10}$)$R^{11}$; or —$C_1$-$C_4$-alkylene-SO$_2$N($R^{10}$)$R^{11}$; wherein each of $R^{10}$ and $R^{11}$ independently is hydrogen; OH; $C_1$-$C_8$alkyl; $C_2$-$C_8$alkenyl; $C_2$-$C_8$alkenyloxy; halo-$C_2$-$C_8$alkenyloxy; $C_3$-$C_8$cycloalkyl; $C_3$-$C_8$cycloalkyl-$C_1$-$C_8$alkyl; $C_1$-$C_8$alkoxy$C_1$-$C_8$alkyl; hydroxy$C_1$-$C_8$alkoxy$C_1$-$C_8$alkyl; hydroxy$C_1$-$C_8$alkyl; ($C_1$-$C_8$alkyl)-carbonyl; aryl$C_1$-$C_8$alkyl which optionally may be substituted on the ring by hydroxy, $C_1$-$C_8$alkoxy, carboxy or $C_2$-$C_8$alkoxycarbonyl; or 5 to 10 membered heterocyclic ring;
or $R^1$ and $R^2$ form together with the C-atoms to which they are attached aryl or a 5 to 10 membered heteroaryl residue comprising one or two heteroatoms selected from N, O and S;
or $R^1$ and $R^2$ form together with the C-atoms to which they are attached a 5 to 15 membered non-aromatic carbocyclic or heterocyclic residue, wherein the heterocyclic residue comprises 1 to 5 heteroatoms selected from N, O and S;
each of $R^5$ and $R^6$ independently is hydrogen; halogen; cyano; $C_1$-$C_8$alkyl; halo-$C_1$-$C_8$alkyl; $C_2$-$C_8$alkenyl; $C_2$-$C_8$alkynyl; $C_3$-$C_8$cycloalkyl; $C_3$-$C_8$cycloalkyl$C_1$-$C_8$alkyl; $C_5$-$C_{10}$aryl$C_1$-$C_8$alkyl; and
(I) at least one of $R^7$, $R^8$ and $R^9$ is:
 (i) halogen; or
 (ii) tetrahydropyran-2-ylmethoxy, tetrahydrofuran-2-ylmethoxy, thiazol-2-ylmethoxy, 2-(2-oxo-pyrrolidin-1-yl)-ethoxy, 3-pyridylmethoxy or phenyl; or
 (iii) 2-hydroxy-ethylamino, piperazin-1-yl, 4-isopropyl-piperazin-1-yl, 4-(2-methoxyethyl)-piperazin-1-yl, 4-phenyl-piperazin-1-yl or 4-acetyl-piperazin-1-yl; or
 (iv) $C_1$-$C_9$alkylsulfanyl; or
 (v) $C_1$-$C_8$alkoxy$C_1$-$C_8$alkoxy$C_1$-$C_8$alkoxy;
 or
(II) $R^7$ and $R^8$ or $R^8$ and $R^9$, respectively form together with the carbon atoms to which they are attached:
 (a) a 5 membered heterocyclic ring comprising 2 nitrogen atoms, wherein the heterocyclic ring is substituted by halogen, 2-dimethylamino-ethyl or 2,2,2-trifluoro-ethyl; or
 (b) a 5 or 6 membered heterocyclic ring comprising 1 nitrogen atom; or
 (c) a 5 to 20 membered heterocyclic residue, wherein the heterocyclic residue comprises 1 to 7 oxygen atoms;
and wherein in (I) up to two, and in (II) up to one of $R^7$, $R^8$ and $R^9$ is hydrogen; hydroxy; $C_1$-$C_8$alkyl; $C_2$-$C_8$alkenyl; halo-$C_1$-$C_8$alkyl; $C_1$-$C_8$alkoxy; $C_3$-$C_8$cycloalkyl; $C_3$-$C_8$cycloalkyl$C_1$-$C_8$alkyl; aryl$C_1$-$C_8$alkyl; —Y—$R^{12}$ wherein Y is a direct bond, O, $C_1$-$C_8$alkylene or —O—(CH$_2$)$_{1-8}$- and $R^{12}$ is a substituted or unsubstituted 5, 6 or 7 membered heterocyclic ring comprising 1, 2 or 3 heteroatoms selected from N, O and S; carboxy; ($C_1$-$C_8$alkoxy)-carbonyl; —N($C_{1-8}$alkyl)-CONR$^{10}$R$^{11}$; —CONR$^{10}$R$^{11}$; —N($R^{10}$)($R^{11}$); —SO$_2$N($R^{10}$)R$^{11}$; or $R^7$ and $R^8$ or $R^8$ and $R^9$, respectively form together with the carbon atoms to which they are attached, a 5 or 6 membered heteroaryl comprising 1, 2 or 3 heteroatoms selected from N, O and S, or a 5 or 6 membered carbocyclic ring;
or
(III) each of $R^7$, $R^8$ and $R^9$ is independently hydrogen; hydroxy; halogen; $C_1$-$C_8$alkyl; $C_2$-$C_8$alkenyl; halo-$C_1$-$C_8$alkyl; $C_1$-$C_8$alkylsulfanyl; $C_1$-$C_8$alkoxy; $C_1$-$C_8$alkoxy$C_1$-$C_8$alkoxy; $C_1$-$C_8$alkoxy$C_1$-$C_8$alkoxy$C_1$-$C_8$alkoxy; $C_3$-$C_8$cycloalkyl; $C_3$-$C_8$cycloalkyl$C_1$-$C_8$alkyl; aryl$C_1$-$C_8$alkyl; —Y—$R^{12}$ wherein Y is a direct bond, O, $C_1$-$C_8$alkylene or —O—(CH$_2$)$_{1-8}$- and $R^{12}$ is a substituted or unsubstituted 5, 6 or 7 membered heterocyclic ring comprising 1, 2 or 3 heteroatoms selected from N, O and S; carboxy; ($C_1$-$C_8$alkoxy)-carbonyl; —N($C_{1-8}$alkyl)-CO—NR$^{10}$R$^{11}$;
—CONR$^{10}$R$^{11}$; —N($R^{10}$)($R^{11}$); SO$_2$N($R^{10}$)R$^{11}$; or $R^7$ and $R^8$ or $R^8$ and $R^9$, respectively form together with the carbon atoms to which they are attached, a 5 or 6 membered heteroaryl or heterocyclic residue comprising 1, 2 or 3 heteroatoms selected from N, O and S, or a 5 or 6 membered carbocyclic ring, or a 7 to 20 membered heterocyclic residue comprising 1 to 7 oxygen atoms; and
(A) Z is $=CR^2$— and
 (a) $R^1$ and $R^2$ form together with the C-atoms to which they are attached a 5 to 15 membered non-aromatic carbocyclic or heterocyclic residue, wherein the heterocyclic residue comprises 1 to 5 heteroatoms selected from N, O and S; or (b) $R^1$ and $R^2$ together form a residue of formula —C(CH$_3$)=CH—O—, —CH=CH—NH— or N=C(CH$_3$)—C(CH$_3$)=N—; or (c) $R^1$ and $R^2$ together form a residue of formula —CH=N—NH— and $R^3$ is —SO$_2$N(R$^{10}$)R$^{11}$; or (d) $R^2$ is
  (i) fluoro-$C_{1-5}$alkoxy comprising 2 to 5 fluorine atoms; or
  (ii) $C_1$-$C_8$alkoxy$C_1$-$C_8$alkoxy$C_1$-$C_8$alkoxy; or
  (iii) $C_2$-$C_8$alkenyloxy; or
  (iv) halo-$C_2$-$C_8$alkenyloxy; or
  (v) benzyloxy; or
  (vi) —N(CH$_3$)(R$^{13}$), wherein $R^{13}$ is methyl or benzyl; or
  (vii) $C_{1-4}$alkoxy; or (B) Z is =N—;

in free form or salt form.

Any aryl may be phenyl or naphthyl, preferably phenyl. Heteroaryl is an aromatic heterocyclic ring, e.g. a 5 or 6 membered aromatic heterocyclic ring, optionally condensed to 1 or 2 benzene rings and/or to a further heterocyclic ring.

Any heterocyclic residue may be saturated or unsaturated (non-aromatic), optionally condensed to 1 or 2 benzene rings and/or to a further heterocyclic ring, and optionally substituted, e.g. on a ring C or N atom (when present), e.g. as disclosed below.

Examples of heterocyclic or heteroaryl residues include e.g. morpholinyl, piperazinyl, piperidyl, pyrrolidinyl, pyridyl, purinyl, pyrimidinyl, N-methyl-aza-cycloheptan-4-yl, indolyl, indolinyl, quinolinyl, isoquinolinyl, 1,2,3,4-tetrahydroquinolinyl, benzothiazolyl, thiazolyl, imidazolyl, benzimidazolyl, benzoxadiazolyl, benzotriazolyl, indanyl, oxadiazolyl, pyrazolyl, triazolyl, or tetrazolyl. Preferred heterocyclic or heteroaryl residues are morpholinyl, piperazinyl, piperidyl, pyrrolidinyl, pyridyl, N-methyl-aza-cycloheptan-4-yl, thiazolyl, imidazolyl, indolinyl or tetrazolyl.

Any alkyl or alkyl moiety may be linear or branched. $C_{1-8}$alkyl is preferably $C_{1-4}$alkyl. $C_{1-8}$alkoxy is preferably $C_{1-4}$alkoxy. Any alkyl, alkoxy, alkenyl, cycloalkyl, heterocyclic residue, aryl or heteroaryl may be, unless otherwise stated, unsubstituted or substituted by one or more substituents selected from halogen; OH; $C_1$-$C_8$alkyl; $C_1$-$C_8$alkoxy; nitro; cyano; COOH; carbamoyl; C(NH$_2$)=NOH; —N(R$^{10}$)R$^{11}$; $C_3$-$C_6$cycloalkyl; 3 to 7 membered heterocyclic ring; phenyl; phenyl-$C_{1-4}$alkyl; 5 or 6 membered heteroaryl. When alkyl, alkoxy or alkenyl is substituted, the substituent is preferably on the terminal C atom. When the heterocyclic residue or heteroaryl is substituted, e.g. as disclosed above, this may be on one or more ring carbon atoms and/or ring nitrogen atom when present. Examples of a substituent on a ring nitrogen atom are e.g. $C_{1-8}$alkyl, carbamoyl, —C(NH$_2$)=NOH, —NR$^{10}$R$^{11}$, $C_{3-6}$cycloalkyl or phenyl-$C_{1-4}$alkyl, preferably $C_{1-4}$alkyl, $C_{3-6}$cycloalkyl or phenyl-$C_{1-4}$alkyl, more preferably $C_{1-4}$alkyl.

Halo-alkyl or halo-alkoxy is alkyl or alkoxy, respectively, wherein one or more H are replaced by halogen, e.g. CF$_3$ or —O—CF$_3$.

Preferably substituted alkyl or alkoxy as $R_7$ is alkyl or alkoxy substituted on the terminal C atom by OH, $C_{1-4}$alkoxy or a heterocyclic ring. When $R^{10}$ or $R^{11}$ is a 5 to 10 membered heterocyclic ring, it may be e.g. thiazolyl.

Halogen may be F, Cl, Br, or I.

When $R^7$ and $R^8$ or $R^8$ and $R^9$ form together with the carbon atoms to which they are attached a 5 or 6 membered carbocyclic ring, this may preferably be cyclopentyl or cyclohexyl.

Preferably at most one of $R^1$, $R^2$ or $R^3$ is CONR$^{10}$R$^{11}$ or SO$_2$NR$^{10}$R$^{11}$, more preferably SO$_2$NR$^{10}$R$^{11}$.

In formula I the following significances are preferred independently, collectively or in any combination or sub-combination:

(a) Z is =CR$^2$;

(b) $R^0$ is hydrogen; halogen, e.g. Cl; unsubstituted $C_1$-$C_4$alkyl, e.g. methyl or ethyl; unsubstituted $C_{1-4}$alkoxy, e.g. methoxy; preferably hydrogen;

(c) $R^1$ is hydrogen; halogen, e.g. Cl or F; OH; $C_1$-$C_8$alkyl, e.g. methyl or ethyl; substituted $C_{1-8}$alkyl, e.g. terminally OH substituted $C_{1-8}$alkyl; —SO$_2$N(R$^{10}$)R$^{11}$; —N($C_{1-4}$alkyl)C(O)$C_{1-4}$alkyl; a 5 or 6 membered heterocyclic ring optionally substituted on a ring N atom (when possible); $C_1$-$C_8$alkoxy, e.g. methoxy; aryl, e.g. phenyl;
  or $R^1$ forms together with $R^2$ and the C-atoms to which $R^1$ and $R^2$ are attached a 5 to 10 membered aryl or heteroaryl, the latter comprising 1 or 2 nitrogen atoms;
  when $R^1$ and $R^2$ form together with the C-atoms to which they are attached a 5 to 15 membered non-aromatic carbocyclic residue, this may preferably be cyclopentyl;
  when $R^1$ and $R^2$ form together with the C-atoms to which they are attached a 5 to 15 membered non-aromatic heterocyclic residue, the residue preferably comprises 1 to 5 O atoms as heteroatoms; the heterocyclic residue may optionally be substituted, e.g. by up to 4 substituents, for example 1 to 4 halogen atoms, e.g. F; more preferably $R^1$ and $R^2$ form part of a 5 or 6 or 7 membered heterocyclic residue comprising 2O atoms, e.g. $R^1$ and $R^2$ together form a residue of formula —O—(CH$_2$)$_3$—O—, —O—(CH$_2$)$_2$—O—, —O—(CF$_2$)$_2$—O—, —O—CH$_2$—O— or —O—CF$_2$—O—, or $R^1$ and $R^2$ form part of a 15 membered heterocyclic residue comprising 5 O atoms, e.g. $R^1$ and $R^2$ together form a residue of formula —O—((CH$_2$)$_2$—O—)$_4$;

(d) $R^2$ is hydrogen; hydroxy; $C_1$-$C_8$alkyl, e.g. methyl or ethyl; substituted $C_{1-8}$alkyl, e.g. terminally OH— or $C_{1-4}$-alkoxy substituted $C_{1-8}$alkyl; $C_{1-8}$alkoxy; $C_1$-$C_4$alkoxy$C_1$-$C_8$alkoxy; —CON(R$^{10}$)R$^{11}$; —SO$_2$N(R$^{10}$)R$^{11}$; fluoro-$C_{1-5}$ alkoxy comprising 2 to 5 fluorine atoms; $C_1$-$C_8$alkoxy$C_1$-$C_8$alkoxy$C_1$-$C_8$alkoxy; $C_2$-$C_8$alkenyloxy; halo-$C_2$-$C_8$alkenyloxy; benzyloxy; or N(CH$_3$)(R$^{13}$), wherein $R^{13}$ is methyl or benzyl;
  when $R^2$ is as defined in (III)(A)(d)(i) above, fluoro-$C_{1-5}$ alkoxy is preferably O—CF$_3$, —O—CH$_2$—CF$_3$ or —O—(CH$_2$)$_3$—CF$_2$—CF$_3$;
  when $R^2$ is as defined in (III)(A)(d)(ii) above, $C_1$-$C_8$alkoxy$C_1$-$C_8$alkoxy$C_1$-$C_8$alkoxy is preferably —O—(CH$_2$)$_2$—O—(CH$_2$)$_2$—O—CH$_3$;
  when $R^2$ is as defined in (III)(A)(d)(iii) above, $C_2$-$C_8$alkenyloxy is preferably $C_2$-$C_4$alkenyloxy, e.g. prop-2-enyloxy;
  when $R^2$ is as defined in (III)(A)(d)(iv) above, halo-$C_2$-$C_8$alkenyloxy is preferably halo-$C_2$-$C_4$alkenyloxy comprising 1 to 3 halogen atoms, e.g. Cl or F, more preferably halo-prop-2-enyloxy, e.g. 2-chloroprop-2-enyloxy, 2-fluoroprop-2-enyloxy, 1,1,2-trifluoroprop-2-enyloxy or 2,3,3-trifluoroprop-2-enyloxy;

(e) $R^3$ is hydrogen; halogen, e.g. Cl, Br; hydroxy; $C_1$-$C_8$alkyl, e.g. methyl or ethyl; substituted $C_{1-8}$alkyl, e.g. terminally OH substituted $C_{1-8}$alkyl; carboxy; CONR$^{10}$R$^{11}$; —SO$_2$N(R$^{10}$)R$^{11}$; a 5 or 6 membered heterocyclic ring optionally substituted on a ring nitrogen atom (when possible); or forms together with $R^4$ and the N and C atoms to which $R^3$ and $R^4$ are attached a 6 membered heterocyclic ring; more preferably $R^3$ is CONR$^{10}$R$^{11}$ more preferably SO$_2$NR$^{10}$R$^{11}$; more preferably SO$_2$NR$_2$;

(f) $R^4$ is hydrogen; or forms together with $R^3$ and the N and C atoms to which $R^3$ and $R^4$ are attached a 6 membered heterocyclic ring; preferably hydrogen;
(g) $R^5$ is hydrogen; halogen; $C_{1-4}$alkyl; or $CF_3$;
(h) $R^6$ is hydrogen;
(i) one of $R^{10}$ and $R^{11}$, independently, is hydrogen or $C_{1-4}$alkyl and the other is hydrogen; $C_{1-8}$-alkyl, substituted $C_{1-8}$alkyl, e.g. terminally substituted by OH, $C_{3-6}$-cycloalkyl or a heterocyclic ring; $C_{2-8}$alkenyl; $C_{3-8}$cycloalkyl; $C_{1-8}$alkoxy$C_{1-4}$alkyl; hydroxy$C_{1-8}$alkoxy$C_{1-8}$alkyl; or a 5 membered heterocyclic ring.

The following significances are preferred independently, collectively or in any combination or sub-combination (including in any combination with the preferred significances given above), for $R^7$, $R^8$ and $R^9$ in each case where they are as defined at (I) to (III) above:

(I) (i) $R^7$ or $R^8$ is halogen; halogen is fluoro, chloro or bromo; $R^7$ is methoxy, $R^8$ is fluoro and $R^9$ is hydrogen; $R^7$ is chloro, $R^8$ is fluoro and $R^9$ is hydrogen; $R^7$ is trifluoromethyl, $R^8$ is chloro and $R^9$ is hydrogen; $R^7$ is bromo and $R^8$ and $R^9$ are each hydrogen;
(ii) $R^7$ is tetrahydropyran-2-ylmethoxy, tetrahydrofuran-2-ylmethoxy, thiazol-2-ylmethoxy, 2-(2-oxo-pyrrolidin-1-yl)-ethoxy, 3-pyridylmethoxy or phenyl, and optionally $R^8$ and $R^9$ are each hydrogen; $R^7$, $R^8$ or $R^9$ is tetrahydropyran-2-ylmethoxy or tetrahydrofuran-2-ylmethoxy;
(iii) $R^7$ is 2-hydroxy-ethylamino, and optionally $R^8$ is hydroxymethyl and $R^9$ is hydrogen; $R^7$ is piperazin-1-yl, 4-isopropyl-piperazin-1-yl, 4-(2-methoxyethyl)-piperazin-1-yl, 4-phenyl-piperazin-1-yl or 4-acetyl-piperazin-1-yl and optionally $R^8$ and $R^9$ are hydrogen;
(iv) $R^8$ is $C_1$-$C_8$alkylsulfanyl; $C_1$-$C_9$alkylsulfanyl is e.g. methylsulfanyl; $R^7$ is methoxy, $R^8$ is methylsulfanyl and $R^9$ is hydrogen;
(v) $R^7$ is $C_1$-$C_8$alkoxy$C_1$-$C_8$alkoxy$C_1$-$C_8$alkoxy; $C_1$-$C_8$alkoxy$C_1$-$C_8$alkoxy$C_1$-$C_8$alkoxy is e.g. 2-(2-methoxy-ethoxy)-ethoxy; $R^7$ is 2-(2-methoxy-ethoxy)-ethoxy, $R^8$ is methoxy or hydrogen and $R^9$ is hydrogen;

(II) (a) $R^8$ and $R^9$ together form a residue of formula —C(Cl)=N—NH—, —CH=N—N(—(CH$_2$)$_2$—N(CH$_3$)$_2$)— or —CH=N—N(—CH$_2$—CF$_3$)— and optionally $R^7$ is hydrogen;
(b) $R^8$ and $R^9$ together form a residue of formula N=CH—CH=CH— and optionally $R^7$ is methoxy;
(c) $R^7$ and $R^8$ or $R^8$ and $R^9$, preferably $R^8$ and $R^9$, form together with the carbon atoms to which they are attached:
(i) a 6 to 9 membered heterocyclic ring comprising 2 oxygen atoms, more preferably wherein each oxygen atom is directly adjacent to the aromatic ring to which $R^7$ and $R^8$ or $R^8$ and $R^9$ are attached, e.g. $R^7$ and $R^8$ or $R^8$ and $R^9$ together form a residue of formula —O—(CH$_2$)$_n$—O— wherein n is 2, 3, 4 or 5; or
(ii) a heterocyclic ring comprising m oxygen atoms and 2m carbon atoms, wherein m is 3, 4 or 5, e.g. $R^7$ and $R^8$ or $R^8$ and $R^9$ together form a residue of formula —(O—CH$_2$—CH$_2$)$_{m-1}$—O—;

(III) $R^7$ is hydrogen; hydroxy; $C_{1-4}$alkyl; substituted $C_{1-4}$alkyl, e.g. terminally OH substituted $C_{1-4}$alkyl; $C_{1-8}$alkoxy; substituted $C_{1-8}$alkoxy, e.g. terminally substituted by OH, $C_{1-4}$alkoxy or a heterocyclic ring; NR$^{10}$R$^{11}$; —SO$_2$N(R$^{10}$)R$^{11}$; —Y—R$^{12}$; CF$_3$; or $R^7$ forms together with $R^8$ and the C-atoms to which $R^7$ and $R^8$ are attached a 5 membered heteroaryl residue, e.g. bridged by —NH—CH=CH—, —CH=CH—NH—, —NH—N=CH—, —CH=N—NH—, —NH—N=N— or N=N—NH—;

$R^8$ is hydrogen; hydroxy; $C_{1-4}$alkoxy; $C_{1-4}$alkyl; carboxy; a 5 or 6 membered heterocyclic ring optionally substituted on a ring C or N atom; N(C$_{1-4}$alkyl)-CO—NR$^{10}$R$^{11}$; NR$^{10}$R$^{11}$; or forms with $R^7$ or $R^9$ and the C-atoms to which $R^7$ and $R^8$ or $R^8$ and $R^9$, respectively, are attached a 5 membered heteroaryl residue, e.g. bridged by —NH—CH=CH—, —CH=CH—NH—, —NH—N=CH—, —CH=N—NH—, —NH—N=N— or N=N—NH—;

$R^9$ is hydrogen; $C_{1-4}$alkoxy; NR$^{10}$R$^{11}$; or forms with $R^8$ and the C atoms to which $R^8$ and $R^9$ are attached a 5 membered heteroaryl, e.g. bridged by —NH—CH=CH—, —CH=CH—NH—, NH—N=CH—, —CH=N—NH—, —NH—N=N— or —N=N—NH—.

According to one preferred embodiment of the invention, $R^3$ is SO$_2$NR$^{10}$R$^{11}$. Preferably Z is =CR$^2$. $R^2$ preferably is $C_{1-4}$alkoxy. More particularly one of $R^7$, $R^8$ and $R^9$ is NR$^{10}$R$^{11}$ and one of the others is H, halogen, COOH, CF$_3$ or $C_{1-4}$alkyl. The third substituent is preferably H. Alternatively, $R^7$ and $R^8$ or $R^8$ and $R^9$, respectively, form together with the carbon atoms to which they are attached, a 5 or 6 membered heteroaryl or heterocyclic residue comprising 1, 2 or 3 heteroatoms.

According to an alternative embodiment of the invention, $R^3$ is SO$_2$NR$^{10}$R$^{11}$, Z is =CR$^2$ and $R^1$ and $R^2$ form together with the C atoms to which they are attached a 5 to 15 membered heterocyclic residue comprising 1 to 5O atoms. Preferably $R^1$ and $R^2$ form part of a 5 or 6 or 7 membered heterocyclic residue comprising 2O atoms, e.g. $R^1$ and $R^2$ together form a residue of formula —O—(CH$_2$)$_n$—O— wherein n is 2, 3, 4 or 5, e.g. —O—(CH$_2$)$_3$—O—, —O—(CH$_2$)$_2$—O—, —O—CH$_2$—O—, or —O—CF$_2$—O— or —O—(CF$_2$)$_2$—O—. Each of $R^7$, $R^8$ and $R^9$ has one of the significances as defined in III. More particularly one of $R^7$, $R^8$ and $R^9$ is NR$^{10}$R$^{11}$ and one of the 2 others is H, halogen, COOH, CF$_3$ or $C_{1-4}$alkyl. The third substituent is preferably H.

The compounds of the invention may exist in free form or in salt form, e.g. addition salts with e.g. organic or inorganic acids, for example trifluoroacetic acid or hydrochloride acid, or salts obtainable when they comprise a carboxy group, e.g. with a base, for example alkali salts such as sodium, potassium, or substituted or unsubstituted ammonium salts.

The present invention also provides a process for the production of a compound of formula I, comprising
a) reacting a compound of formula II

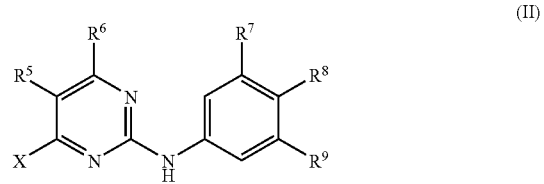

wherein $R^5$, $R^6$, $R^7$, $R^8$ and $R^9$ are as defined above, and X is a leaving group, preferably halogen such as chloride, bromide or iodide, or methylsulfanyl;

with a compound of formula III

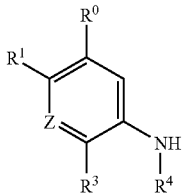

(III)

wherein $R^0$, $R^1$, $R^3$, $R^4$, and Z are as defined above; or b) reacting a compound of formula IV

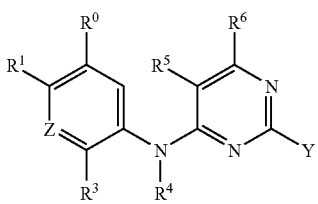

(IV)

wherein $R^0$, $R^1$, $R^3$, $R^4$, $R^5$, $R^6$ and Z are as defined above and Y is a leaving group, preferably halogen such as chloride, bromide or iodide, or methylsulfanyl, with a compound of formula V

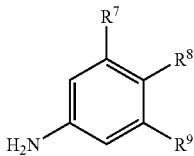

(V)

wherein $R^7$, $R^8$ and $R^9$ are as defined above;

and recovering the resulting compound of formula I in free or in form of a salt, and, where required, converting the compound of formula I obtained in free form into the desired salt form, or vice versa.

The process may be performed according to methods known in the art, e.g. as described in the examples hereinafter. When $R^9$ is or comprises —$NR^{10}R^{11}$ wherein at least one of $R^{10}$ and $R^{11}$ is H, it is preferable to use a compound of formula (V) wherein $R^9$ comprises a protecting group, e.g. a conventional amino protecting group. When such a protecting group is present, it is then removed at the end of the synthesis.

The compound of formula II used as starting material may be obtained by converting a corresponding compound of formula IIa

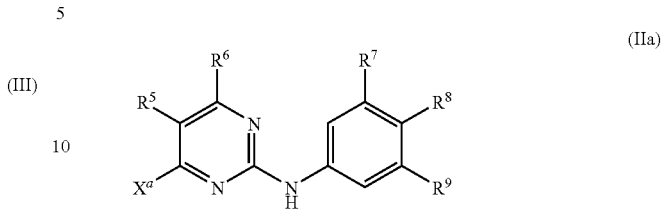

(IIa)

wherein $R^5$, $R^6$, $R^7$, $R^8$ and $R^9$ are as defined above, and $X^a$ is hydroxy,
to a compound of formula II, e.g. using known methods, for example as described in example 1.

The compound of formula IIa used as starting material may be obtained by reacting a compound of formula VI

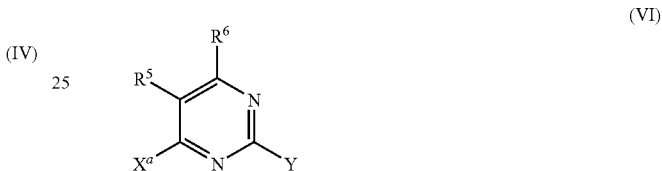

(VI)

wherein $R^5$, $R^6$, $X^a$ and Y are as defined above, with a compound of formula V as defined above.

The compound of formula IV used as starting material may be obtained by reacting a compound of formula III as defined above with a compound of formula VII

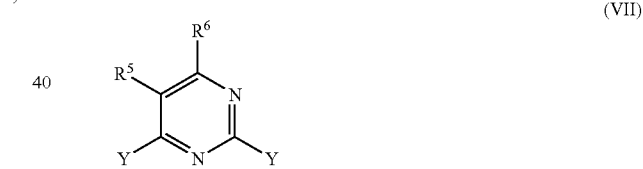

(VII)

wherein $R^5$ and $R^6$ are as defined above and Y is a leaving group as defined above, preferably a chloride.

The compounds of formulae IV, V and VI are known, or may be produced in accordance with known procedures, procedures described in the examples or procedures analogous thereto.

The production of a compound wherein $R^3$ is $SO_2NR^{10}R^{11}$ may be performed e.g. via three alternative routes, e.g. i) by reaction with $ClSO_2N\!\!=\!\!C\!\!=\!\!O$, (ii) by reaction with BuLi, or (iii) by forming a diazonium salt.

According to the invention, a compound of formula IIIa

IIIa wherein R' is $SO_2$—N=CH—$N(CH_3)_2$ and R" is OH, halo-$C_1$-$C_8$alkyl; $C_1$-$C_8$alkoxy; $C_{2-8}$alkenyl-oxy; $C_{2-8}$alkynyl-oxy; halo-$C_1$-$C_8$-alkoxy; hydroxy$C_1$-$C_8$alkoxy; $C_1$-$C_8$alkoxy$C_1$-$C_8$alkoxy; $C_1$-$C_8$alkoxy$C_1$-$C_8$alkoxy$C_1$-$C_8$alkoxy; aryl; aryl$C_1$-$C_8$alkoxy; carboxy; $C_2$-$C_8$alkoxycarbonyl; $C_2$-$C_8$alkylcarbonyl, are novel and also form part of the invention. They are useful as intermediates for the production of compounds of formula II.

The following examples illustrate the invention without any limitation.

The following abbreviations are employed:
DMF=dimethylformamide, DMSO=dimethylsulfoxide; MS=molecular ion (e.g. $M+H^{1+}$) determined by electrospray mass spectroscopy; THF=tetrahydrofuran; TBME=tert-butyl methyl ether.

EXAMPLE 1

6-[2-(3,4,5-Trimethoxy-phenylamino)-pyrimidin-4-ylamino]-2,3-dihydro-benzo[1,4]dioxine-5-sulfonic acid amide

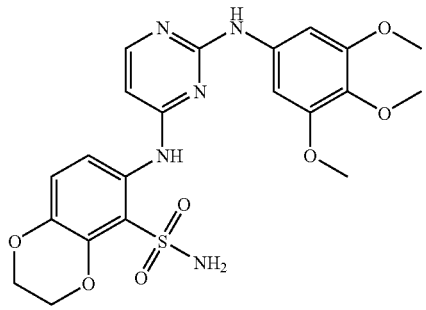

A: (4-Chloro-pyrimidin-2-yl)-(3,4,5-trimethoxy-phenyl)-amine 3,4,5-Trimethoxy-phenylamine (10 g, 54.6 mmol) and 2-methylsulfanyl-pyrimidin-4-ol (7.76 g, 54.6 mmol) are mixed and heated to 150° C. for 2 h whereupon the mixture melts. The evolving gas is absorbed in sodium hypochlorite solution. The remaining residue is suspended in acetonitrile (300 ml). $POCl_3$ (10.8 ml, 117 mmol) and 4 N HCl in dioxane (35.2 ml, 140 mmol) are added and the mixture is heated to 90° C. until the reaction is complete. The mixture is extracted with ethyl acetate, washed with sat. sodium bicarbonate and brine. The organic layer is dried with sodium sulfate and evaporated. The residue is crystallized from methanol to give (4-chloro-pyrimidin-2-yl)-(3,4,5-trimethoxy-phenyl)-amine.

B: 6-Amino-2,3-dihydro-benzo[1,4]dioxine-5-sulfonic acid amide

Under an atmosphere of nitrogen 2,3-dihydro-benzo[1,4]dioxin-6-ylamine (5.0 g, 33.0 mmol) is added dropwise to a solution of chlorsulfonyl isocyanate (3.14 ml, 36.3 mmol) in nitroethane (75 ml) at −55 to −49° C. The cooling bath is removed and the mixture allowed to warm to 0° C., where upon aluminium chloride (5.27 g, 39.6 mmol) is added. Heating the mixture to 120° C. for 30 min forms a clear brown solution, which is cooled to room temperature and poured on ice. After filtration, washing with ice water and diethylether the precipitate is collected.

2 g of the above precipitate are dissolved in 60 ml 50% $H_2SO_4$ to form a dark suspension, which is heated to 130° C. for 2 h. After 2 h the mixture is a clear dark solution. After cooling to room temperature the clear dark solution is poured on ice. The pH is brought to 13 with a cold 40% aqueous solution of NaOH. The aqueous layer is extracted several times with ethyl acetate, washed with water and brine, dryed ($Na_2SO_4$) and concentrated to yield a brown solid, which is a 10:1 mixture of isomers (undesired to desired). The mixture of isomers is separated by chromatography on silica gel using cyclohexane/ethyl acetate (50:50 v/v) to yield 6-amino-2,3-dihydro-benzo[1,4]dioxine-5-sulfonic acid amide as a white solid.

C: 6-[2-(3,4,5-Trimethoxy-phenylamino)-pyrimidin-4-ylamino]-2,3-dihydro-benzo[1,4]dioxine-5-sulfonic acid amide 6-Amino-2,3-dihydro-benzo[1,4]dioxine-5-sulfonic acid amide (87 mg, 0.38 mmol) and (4-chloro-pyrimidin-2-yl)-(3,4,5-trimethoxy-phenyl)-amine (112 mg, 0.38 mmol) are dissolved in dioxane (1.3 ml). The mixture is heated to 120° C. for 1 h. The reaction mixture is purified by repeated chromatography on silica gel using different solvent mixture, yielding 6-[2-(3,4,5-trimethoxy-phenylamino)-pyrimidin-4-ylamino]-2,3-dihydro-benzo[1,4]dioxine-5-sulfonic acid amide.

MS (ESI): 490 $[M+H]^+$

EXAMPLE 2

5-[2-(3,4-Dimethoxy-phenylamino)-pyrimidin-4-ylamino]-benzo[1,3]dioxole-4-sulfonic acid amide

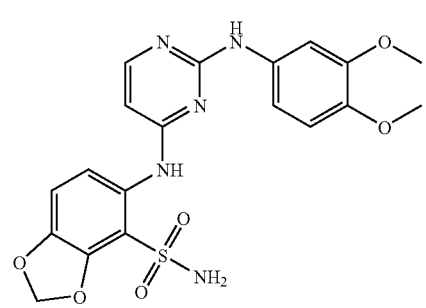

A: (4-Chloro-pyrimidin-2-yl)-(3,4-dimethoxy-phenyl)-amine (4-Chloro-pyrimidin-2-yl)-(3,4-dimethoxy-phenyl)-amine is prepared as described for example 1 step A using 3,4-dimethoxy-phenylamine instead of 3,4,5-trimethoxy-phenylamine.

B: 2-Allyloxy-6-amino-benzenesulfonamide

To a solution of 1,3-benzodioxol-5-amine (10 g, 73 mmol) in 200 ml $Et_2O$ and 100 ml THF, $NEt_3$ (12.3 ml, 87.6 mmol) is added. The reaction mixture is cooled to 0° C. and pivaloyl chloride (10.5 ml, 87.6 mmol) in THF is added. After stirring for 1 h at 25° C., ice water is added, the mixture extracted with EtOAc and washed with brine, followed by drying ($Na_2SO_4$), evaporation of volatiles, and crystallization (CH₂Cl₂/hexanes) which gives N-benzo[1,3]dioxol-5-yl-2,2-dimethyl-propionamide.

To a solution of N-benzo[1,3]dioxol-5-yl-2,2-dimethyl-propionamide (1.8 g, 8.0 mmol) in dry THF (20 ml) n-butyl lithium (20 ml, 1.6 M in hexanes, 32 mmol) is added within 5 min at −60 to −45° C. (Argon). After stirring for 1 h at 5° C., the solution is cooled down to −60° C. and SO₂ (1.8 g, 35 mmol) in dry ether (20 ml) is added. The mixture is slowly warmed to 0° C., stirred for 30 min, and poured into an excess of diethyl ether. The precipitate is collected by filtration and washed with ether. This precipitate (4.0 g) is dissolved in water (40 ml). After the addition of NaOAc (5.6 g, 70 mmol), hydroxylamine-O-sulfonic acid (3.8 g, 35 mmol) is added. The reaction mixture is stirred at 25° C. for 1 h, the precipitate collected by filtration, washed with water and dried, yielding 2,2-dimethyl-N-(4-sulfamoyl-benzo[1,3]dioxol-5-yl)-propionamide.

A solution of 2,2-dimethyl-N-(4-sulfamoyl-benzo[1,3]dioxol-5-yl)-propionamide (800 mg, 2.7 mmol) in 1,2 dimethoxyethan (15 ml) and conc. HCl (15 ml) is stirred at 90° C. for 5 h. The pH is adjusted to 10, the mixture extracted with EtOAc and washed with brine, followed by drying (Na₂SO₄), evaporation of volatiles and crystallization (CH₂Cl₂/MeOH) which affords 5-amino-benzo[1,3]dioxole-4-sulfonic acid amide.

C: 5-[2-(3,4-Dimethoxy-phenylamino)-pyrimidin-4-ylamino]-benzo[1,3]dioxole-4-sulfonic acid amide 5-[2-(3,4-Dimethoxy-phenylamino)-pyrimidin-4-ylamino]-benzo[1,3]dioxole-4-sulfonic acid amide is prepared as described in example 1 step C by using 4-chloro-pyrimidin-2-yl)-(3,4-dimethoxy-phenyl)-amine and 5-amino-benzo[1,3]dioxole-4-sulfonic acid amide.
MS (ESI): 446.1 [M+H]⁺, 444.1 [M−H]⁺.

EXAMPLE 3

5-[2-(3,4,5-Trimethoxy-phenylamino)-pyrimidin-4-ylamino]-indan-4-sulfonic acid amide

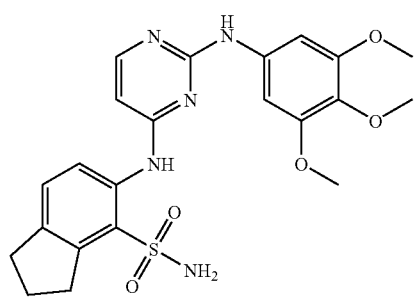

A: (4-Chloro-pyrimidin-2-yl)-(3,4,5-trimethoxy-phenyl)-amine

As described for example 1, step A.

B: 5-Amino-indan-4-sulfonic acid amide

5-Amino-indan-4-sulfonic acid amide is prepared as described for example 1 step B using indan-5-ylamine instead of 2,3-dihydro-benzo[1,4]dioxin-6-ylamine as the starting material.

C: 5-[2-(3,4,5-Trimethoxy-phenylamino)-pyrimidin-4-ylamino]-indan-4-sulfonic acid amide (4-Chloro-pyrimidin-2-yl)-(3,4,5-trimethoxy-phenyl)-amine (240 mg, 0.81 mmol) and 5-amino-indan-4-sulfonic acid amide (190 mg, 0.89 mmol) are suspended in isopropanol (15 ml). Conc. HCl (1.5 ml) is added. The mixture is heated to reflux for 1 h. The reaction mixture is separated between ethyl acetate (300 ml) and water (100 ml). NaHCO₃ is added to achieve basic pH. The layers are separated. The organic layer is dried with Na₂SO₄ and evaporated. The residue is crystallized from ethyl acetate to give 5-[2-(3,4,5-trimethoxy-phenylamino)-pyrimidin-4-ylamino]-indan-4-sulfonic acid amide.
MS (ESI): 472 [(M+H]⁺

EXAMPLE 4

2-(Dimethyl-amino)-6-[2-(3,4,5-trimethoxy-phenylamino)-pyrimidin-4-ylamino]-benzenesulfonamide

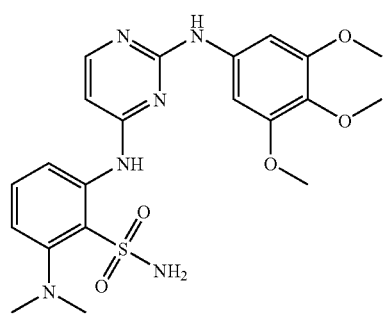

A: (4-Chloro-pyrimidin-2-yl)-(3,4,5-trimethoxy-phenyl)-amine

As described for example 1, step A.

B: 2-Amino-6-dimethylamino-benzenesulfonamide

Phenyl-methanethiol (12.0 ml, 100 mmol) is added dropwise to a mixture of 1,2-dichloro-nitrobenzene (23.0 g, 120 mmol), Bu₄NHSO₄ (1.0 g), CH₂Cl₂ (250 ml) and NaOH (30%, 60 ml) and the mixture stirred at 25° C. for 16 h. Water is added, the organic phase is separated and dried with Na₂SO₄. The solvent is removed to give an orange oil which is dissolved in AcOH (90%, 500 ml). Cl₂ gas is bubbled through the solution until complete consumption is reached. The solvent is removed and the residue subjected to chromatography (SiO₂, TBME/cyclohexane 1:4→TBME). The resulting solid is added portion wise to a mixture of NH₄OH and ethanol (1:1, 150 ml) and the mixture stirred for 2 h at 25° C. Water is added and the resulting precipitate is filtered of. 2-Chloro-6-nitro-benzenesulfonamide is isolated as a colorless solid.

A mixture of 2-chloro-6-nitro-benzenesulfonamide (500 mg, 2.10 mmol), DMSO (3 ml), diethyl amine (10 ml of 2 M solution in THF), Bu₄NHSO₄ (34 mg, 0.1 mmol) and KF (58 mg, 1.0 mmol) is heated in an autoclave at 70° C. for 16 h. The mixture is diluted with water and extracted with CH₂Cl₂. The solvent is removed and the residue subjected to chromatography (SiO$_2$, TBME/cyclohexane 1:9→TBME) to give 2-dimethylamino-6-nitro-benzenesulfonamide as a colorless solid.

A mixture of 2-dimethylamino-6-nitro-benzenesulfonamide (753 mg, 3.07 mmol), Pd (10%) on charcoal (100 mg) and methanol (25 ml) is hydrogenated at 25° C. for 2 h. Pd is removed by filtration, the solvent evaporated and the residue crystallized from TBME/cyclohexane to give 2-amino-6-dimethylamino-benzenesulfonamide as a colorless solid.

C: 2-(Dimethyl-amino)-6-[2-(3,4,5-trimethoxy-phenylamino)-pyrimidin-4-ylamino]-benzenesulfonamide 2-(Dimethyl-amino)-6-[2-(3,4,5-trimethoxy-phenylamino)-pyrimidin-4-ylamino]-benzenesulfonamide is prepared as described in Example 1 step C by using 4-chloro-pyrimidin-2-yl)-(3,4,5-trimethoxy-phenyl)-amine (example 1 step A) and 2-amino-6-dimethylamino-benzenesulfonamide.

MS (ESI): 475 [M+H$^+$]$^+$

EXAMPLE 5

2-Allyloxy-6-[2-(3,4-dimethoxy-phenylamino)-pyrimidin-4-ylamino]-benzenesulfonamide

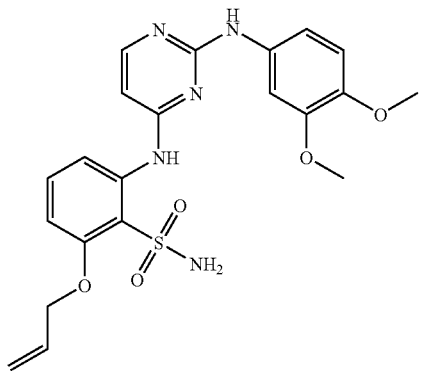

A: (4-Chloro-pyrimidin-2-yl)-(3,4-dimethoxy-phenyl)-amine (4-Chloro-pyrimidin-2-yl)-(3,4-dimethoxy-phenyl)-amine is prepared as described for example 1 step A using 3,4-dimethoxy-phenylamine instead of 3,4,5-trimethoxy-phenylamine.

B: 2-Allyloxy-6-amino-benzenesulfonamide

To a solution of 3-amino-phenol (60 g, 6.55 mol) in 2 N NaOH (1 l), cooled to 10° C., pivaloyl chloride (68 ml, 0.55 mol) in toluene (200 ml) is added within 1 h. After stirring for 15 h at 25° C., the mixture is cooled to 0° C. and acidified to pH 1 with conc. HCl. Extraction with EtOAc washing with water, 10% NaHCO$_3$, water, and brine, followed by drying (Na$_2$SO$_4$), evaporation of volatiles, and crystallization (EtOAc/hexanes) gives N-(3-hydroxy-phenyl)-2,2-dimethyl-propionamide. N-(3-Hydroxy-phenyl)-2,2-dimethyl-propionamide (49 g, 0.254 mol) in dichloromethane (1 l) is treated with dihydropyrane (66 ml, 0.762 mol) and pyridinium p-toluenesulfonate (957 mg, 3.8 mmol). After stirring for 6 days at 25° C., the solvent is removed and the residue crystallized from EtOAc/hexanes to give 2,2-dimethyl-N-[3-(tetrahydro-pyran-2-yloxy)-phenyl]-propionamide.

To a solution of 2,2-dimethyl-N-[3-(tetrahydro-pyran-2-yloxy)-phenyl]-propionamide (57.7 g, 208 mmol) in dry THF (500 ml) n-butyl lithium (325 ml, 1.6 M in hexanes, 521 mmol) are added within 5 min at −55 to −20° C. (Argon). After stirring for 1 h dry ether (400 ml) is added, followed by liquid SO$_2$ (100 g) at −55° C. The mixture is slowly warmed to 25° C. and poured into an excess of diethyl. The precipitate is collected by filtration and washed with ether. This precipitate (84 g) is dissolved in water (440 ml). After the addition of NaOAc (85.5 g, 1.04 mol) and cooling to 15° C., hydroxylamine-O-sulfonic acid (58.8 g, 0.52 mol) is added in portions within 20 min, keeping the temperature below 20° C. Stirring at 25° for 15 h is followed by extraction with EtOAc. The organic layer is dried (Na$_2$SO$_4$) and evaporated. Chromatography (silica gel, hexanes/AcOEt, various ratios) gives 2,2-dimethyl-N-[2-sulfamoyl-3-(tetrahydro-pyran-2-yloxy)-phenyl]-propionamide and N-(3-hydroxy-2-sulfamoyl-phenyl)-2,2-dimethyl-propionamide (cf. below, cleavage of tetrahydropyranyloxy).

To a solution of 2,2-dimethyl-N-[2-sulfamoyl-3-(tetrahydro-pyran-2-yloxy)-phenyl]-propionamide (21.9 g, 61.5 mmol) in methanol (220 ml) a solution of methanesulfonic acid (11 ml) in methanol (10 ml) is added within 4 min at 25° C. After stirring for 1 h, the solvent is removed. The residue is partitioned between water and EtOAc. After washings with water, 10% NaHCO$_3$, and brine, evaporation of the dried (Na$_2$SO$_4$) organic phase gave N-(3-hydroxy-2-sulfamoyl-phenyl)-2,2-dimethyl-propionamide.

A solution of N-(3-hydroxy-2-sulfamoyl-phenyl)-2,2-dimethyl-propionamide (15.2 g, 55.9 mmol) and N,N-dimethylformamide dimethylacetal (9.7 ml, 72.6 mmol) in DMF (65 ml) is stirred at 60° C. for 1 h. Volatiles are evaporated at reduced pressure. Chromatography of the residue (21.8 g) dissolved in dichloromethane (silica gel, hexanes/EtOAc=1:1) gives N-(2-{[1-dimethylamino-meth-(E)-ylidene]-sulfamoyl}-3-hydroxy-phenyl)-2,2-dimethyl-propionamide.

A solution of N-(2-{[1-dimethylamino-meth-(E)-ylidene]-sulfamoyl}-3-hydroxy-phenyl)-2,2-dimethyl-propionamide (600 mg, 1.84 mmol) in DMF (4 ml) is treated at 70° C. with allyl bromide (217 µl, 2.57 mmol) and K$_2$CO$_3$ (380 mg) for 45 min with stirring. After evaporation of the solvent, the residue is partitioned between water and EtOAc. The organic layer is dried (Na$_2$SO$_4$) and evaporated yielding N-(3-allyloxy-2-{[1-dimethylamino-meth-(E)-ylidene]-sulfamoyl}-phenyl)-2,2-dimethyl-propionamide. A solution of N-(3-allyloxy-2-{[1-dimethylamino-meth-(E)-ylidene]-sulfamoyl}-phenyl)-2,2-dimethyl-propionamide (387 mg, 1.05 mmol) in ethanol (12 ml) and 12 drops of conc HCl (aprox. 0.2 ml) is refluxed for 36 h. After evaporation of the solvent, the residue is partitioned between ammonia (pH 10 to 11) and EtOAc. The organic layer is dried (Na$_2$SO$_4$) and evaporated. Chromatography (silica gel, EtOAc/hexanes=2:1) afforded N-(3-allyloxy-2-sulfamoyl-phenyl)-2,2-dimethyl-propionamide containing some N-(3-allyloxy-2-sulfamoyl-phenyl)-2,2-dimethyl-propionamide. Treatment of this material with ethanol (20 ml) and conc. HCl (2 ml) for 30 h at reflux temperature and workup as above gives N-(3-allyloxy-2-sulfamoyl-phenyl)-2,2-dimethyl-propionamide.

C: 2-Allyloxy-6-[2-(3,4-dimethoxy-phenylamino)-pyrimidin-4-ylamino]-benzenesulfonamide A solution of 6-Allyloxy-2-aminophenyl-sulfonamide (38 mg, 0.166 mmol) and 4-chloro-2-(3,4-dimethoxy-phenylamino)pyrimidine (44.2 mg, 0.166 mmol) in 2-propanol (5 ml) and 1N HCl (333 μl) is refluxed for 105 min. The reaction mixture is partitioned between ammonia (pH 10-11) and EtOAc. The organic layer is dried (Na$_2$SO$_4$) and concentrated. Precipitation with ether/hexanes gives the desired 2-Allyloxy-6-[2-(3,4-dimethoxy-phenylamino)-pyrimidin-4-ylamino]-benzenesulfonamide.

MS (ESI): 458 ([M+H]$^+$), 456 ([M−H]$^+$).

EXAMPLE 6

2-[2-(3,4-Dimethoxy-phenylamino)-pyrimidin-4-ylamino]-6-trifluoromethoxy-benzenesulfonamide

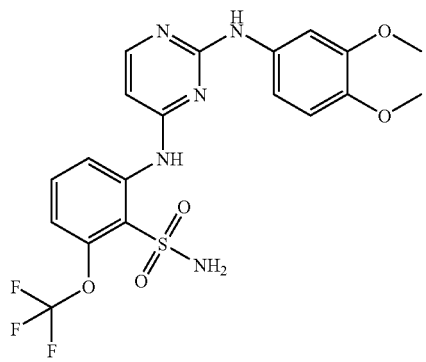

A: (4-Chloro-pyrimidin-2-yl)-(3,4-dimethoxy-phenyl)-amine (4-Chloro-pyrimidin-2-yl)-(3,4-dimethoxy-phenyl)-amine is prepared as described for example 1 step A using 3,4-dimethoxy-phenylamine instead of 3,4,5-trimethoxy-phenylamine.

B: 2-Amino-6-trifluoromethoxy-benzenesulfonamide

To a solution of 3-trifluoromethoxy nitrobenzene (4.0 g, 20 mmol) in DMSO (60 ml), trimethylhydrazinium iodide (4.4 g, 22 mmol) is added and cooled to 0° C. KOt-Bu is added in 4 portions. After stirring for 4 h at 25° C., ice water is added, pH is adjusted to 2-3 with HCl solution, the mixture extracted with EtOAc and washed with brine, followed by drying (Na$_2$SO$_4$) and evaporation of the solvent. Chromatography (silica gel, CH$_2$Cl$_2$/hexane=1:1) gave 2-nitro-6-trifluoromethoxy-phenylamine.

2-Nitro-6-trifluoromethoxy-phenylamine (1.0 g, 4.5 mmol) is dissolved in AcOH (1 ml) and added to conc. HCl (10 ml). The mixture is cooled to 0° C. and NaNO$_2$ dissolved in water (1 ml) is added, then the solution is stirred for 30 min. After filtration, the solution is added at −5° C. to a emulsion of AcOH (4.5 ml) saturated with SO$_2$ and CuCl$_2$ (180 mg, 1.2 mmol) in water (0.3 ml). After stirring for 1 h, water is added, the mixture extracted with EtOAc and washed with brine, followed by drying (Na$_2$SO$_4$) and evaporation of the solvent. The residue is dissolved in acetonitrile (3 ml) and added to a solution of conc. NH$_3$ (20 ml). After stirring for 2 h, the acetonitrile is removed and the residue extracted with EtOAc, washed with brine, dried (Na$_2$SO$_4$) and the solvent is evaporated. Chromatography (silica gel, CH$_2$Cl$_2$ to CH$_2$Cl$_2$/MeOH=95:5) gave 2-nitro-6-trifluoromethoxy-benzenesulfonamide.

A mixture of 2-nitro-6-trifluoromethoxy-benzenesulfonamide (300 mg, 1.0 mmol), Pd (10%) on charcoal (60 mg), methanol (20 ml) and water (1 ml) is hydrogenated at 25° C. for 3 h. Pd is removed by filtration, the solvent is evaporated and the residue crystallized from diethylether/hexane to give 2-amino-6-dimethylamino-benzenesulfonamide.

C: 2-[2-(3,4-Dimethoxy-phenylamino)-pyrimidin-4-ylamino]-6-trifluoromethoxy-benzenesulfonamide 2-[2-(3,4-Dimethoxy-phenylamino)-pyrimidin-4-ylamino]-6-trifluoromethoxy-benzenesulfon-amide is prepared as described in example 1 step C by using 4-chloro-pyrimidin-2-yl)-(3,4-dimethoxy-phenyl)-amine and 2-amino-6-trifluoromethoxy-benzenesulfonamide.

MS (ESI): 486 [M+H]$^+$.

EXAMPLE 7

6-{2-[3-(2-Methoxy-ethylamino)-4-methyl-phenylamino]-pyrimidin-4-ylamino}-2,3-dihydro-benzo[1,4]dioxine-5-sulfonic acid amide

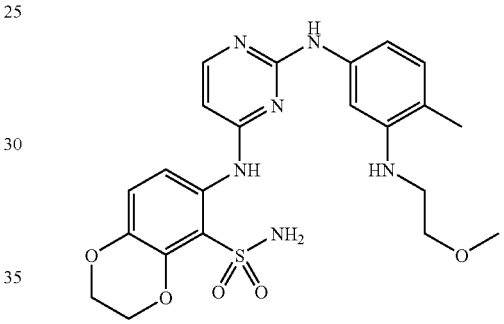

6-(2-Chloro-pyrimidin-4-ylamino)-2,3-dihydro-benzo[1,4]dioxine-5-sulfonic acid amide (151 mg, 0.44 mM) and N*3*-(2-Methoxy-ethyl)-4-methyl-benzene-1,3-diamine (72 mg, 0.40 mM) are suspended in dioxane (1.1 ml). 1N HCl (1.1 ml) is added and the solution is heated to 90° C. for 6 h. After cooling to room temperature, sat. NaHCO$_3$-solution and ethyl acetate are added, the layers are separated and the aqueous phase is extracted several times with ethyl acetate. The combined organic phases are washed with brine, dried over Na$_2$SO$_4$, and the solvent is removed in vacuo. After chromatography (ethyl acetate) the pure product is obtained as white crystals, MH$^+$=487.

N*3*-(2-Methoxy-ethyl)-4-methyl-benzene-1,3-diamine, used as building block in the preparation of the compound of Example 7 may be obtained as follows:

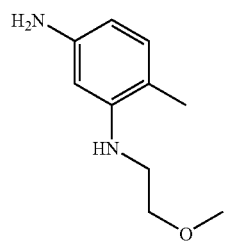

K$_3$PO$_4$ (2.13 g, 10 mM), 3-bromo-4-methylaniline (930 mg, 5 mM), CuI (50 mg, 0.25 mM), and N,N-Diethyl-2- hydroxy-benzamide are mixed and put into an autoklave which has been purged with argon. 2-Methoxyethylamine (3.75 g, 50 mM) is added and the autoclave is heated to 90° C. for 3 d. After cooling to room temperature, $H_2O$ (50 ml), $NH_4OH$ (2.5 ml) and ethyl acetate (50 ml) are added and the layers are separated. The aqueous phase is extracted several times with ethyl acetate. The combined organic phases are washed with brine, dried over $Na_2SO_4$, and the solvent is removed in vacuo. After chromatography (hexane/ethyl acetate=4:2) the pure product is obtained as a brown oil, $MH^+=181$.

Monomethylated aniline building blocks, useful in the synthesis of further compounds of the invention, may be prepared as follows:

2,N-Dimethyl-benzene-1,3-diamine

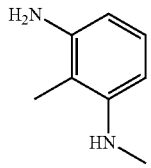

NaH (720 mg, 16.5 mM) is added to a solution of 2-methyl-3-nitroaniline (2.28 g, 15 mM) in THF (10 mL). After stirring at room temperature for 50 min, methyl iodide (4.86 g, 33 mM) is added and the reaction mixture stirred at room temperature overnight. $H_2O$ and ethyl acetate are added, the layers are separated and the aqueous layer is extracted several times with ethyl acetate. The combined organic phases are washed with brine and dried over $Na_2SO_4$. The solvent is removed in vacuo and the residue is purified by chromatography (cyclohexane/$CH_2Cl_2$=4:3) to afford the methylated product as yellow crystalls, $MH^+=167$.

Under an argon atmosphere the crystals above are dissolved in ethanol (15 ml), Pd/C (85 mg, 10%) and sodium borohydride (387 mg, 10.2 mM) are added and the reaction mixture is stirred for 3.5 h at room temperature. After filtration through Celite and removal of the solvent in vacuo, the residue is dissolved in $H_2O$ and ethyl acetate. The layers are separated and the aqueous phase is extracted several times with ethyl acetate. The combined organic phases are washed with brine, dried over $Na_2SO_4$, and the solvent is removed in vacuo. 2,N-Dimethyl-benzene-1,3-diamine is obtained as a black oil, $MH^+=136$.

The compounds of formula $X_1$

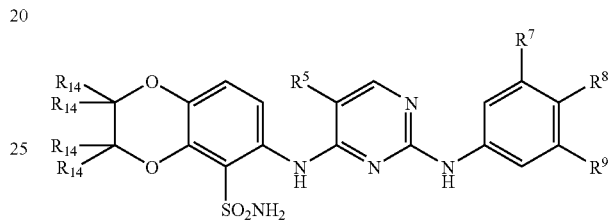

wherein $R^5$, $R^7$, $R^8$, $R^9$ and $R^{14}$ are as defined in Table 1, may be prepared by following one of the above procedures but using the appropriate starting materials.

TABLE 1

| Ex. | $R^5$ | $R^7$ | $R^8$ | $R^9$ | $R^{14}$ | MS Data *ES+ | *ES− | *EI |
|---|---|---|---|---|---|---|---|---|
| 8 | —H | —N(CH$_3$)$_2$ | —OCH$_3$ | —H | —H | 473.2 | 471.3 | |
| 9 | —H | —O—(CH$_2$)$_2$-piperidino | —H | —H | —H | 527.2 | 525.2 | |
| 10 | —H | —H | | —CH═N—NH— | —H | 440.1 | 438.2 | |
| 11 | —H | —O—(CH$_2$)$_2$-(4-methyl-piperazin-1-yl) | —H | —H | —H | 542.2 | 540.3 | |
| 12 | —H | —O—(CH$_2$)$_2$-morpholino | —H | —H | —H | 529.2 | 527.3 | |
| 13 | —Br | —H | | —CH═N—N(CH$_3$)— | —H | 532/534 | | |
| 14 | —H | 4-methyl-piperazin-1-yl | —H | —H | —H | 498 | | |
| 15 | —Br | —O—(CH$_2$)$_2$—OCH$_3$ | —OCH$_3$ | —H | —H | 582/584 | | |
| 16 | —Br | —O—(CH$_2$)$_2$-piperidino | —H | —H | —H | 605/607 | | |
| 17 | —H | —OCH$_3$ | —N(CH$_3$)$_2$ | —H | —H | 473.1 | 471.2 | 472.5 |
| 18 | —F | —OCH$_3$ | —OCH$_3$ | —OCH$_3$ | —H | 508 | | |
| 19 | —H | —O—CH$_2$-(tetrahydro-furan-2-yl) | —H | —H | —H | 500.2 | 498.2 | 499.5 |
| 20 | —H | —N(CH$_2$CH$_3$)$_2$ | —OCH$_3$ | —H | —H | | | |
| 21 | —H | —O—CH$_2$-(5-methyl-isoxazol-3-yl) | —H | —H | —H | 511.1 | 509.2 | 510.5 |
| 22 | —CH$_3$ | —OCH$_3$ | —OCH$_3$ | —OCH$_3$ | —H | | 502 | |
| 23 | —CH$_3$ | —O—(CH$_2$)$_2$-piperidino | —H | —H | —H | | 539 | |
| 24 | —H | —OCH$_3$ | —H | —H | —H | 430.4 | 428.4 | 429.5 |
| 25 | —H | —OCH$_3$ | —C(O)—O—CH(CH$_3$)—CH$_3$ | —H | —H | 516.1 | 514.2 | 515.6 |
| 26 | —H | 4-methyl-piperazin-1-yl | —OCH$_3$ | —H | —H | 528.1 | 526.2 | |
| 27 | —H | —OCH$_3$ | | —(CH)$_4$— | —H | 480.1 | | 479.5 |
| 28 | —H | —OCH$_3$ | | —N═(CH)$_3$— | —H | 481 | | 480.5 |
| 29 | —H | piperidino | —OCH$_3$ | —H | —H | 513.2 | 511.2 | |
| 30 | —H | —OCH$_3$ | —OCH$_3$ | —H | —H | 460.2 | 458.2 | |
| 31 | —H | —H | —H | —H | —H | 400.1 | 398.1 | |
| 32 | —H | —OCH$_3$ | —NH—CH$_3$ | —H | —H | 459.1 | 457.1 | 458.5 |
| 33 | —H | morpholino | —OCH$_3$ | —H | —H | 515.1 | 513.2 | |
| 34 | —H | —O—CH$_2$—C(O)—O—CH(CH$_3$)—CH$_3$ | —H | —H | —H | 516.1 | 514.2 | 515.6 |
| 35 | —H | —O—CH$_2$-(tetrahydro-pyran-2-yl) | —H | —H | —H | 514.1 | 512.2 | 513.6 |
| 36 | —H | —OCH$_3$ | —F | —H | —H | 448.1 | 446.2 | 447.5 |
| 37 | —H | —O—(CH$_2$)$_2$—OCH$_3$ | —OCH$_3$ | —H | —H | 504.1 | 502.2 | |
| 38 | —H | —O—(CH$_2$)$_2$-morpholino | —OCH$_3$ | —H | —H | 559.1 | 557.2 | |
| 39 | —H | —O—(CH$_2$)$_2$-(4-methyl-piperazin-1-yl) | —OCH$_3$ | —H | —H | 572.1 | 570.2 | |
| 40 | —H | —H | | —CH═N—N(CH$_3$)— | —H | | 452 | |
| 41 | —H | —O—CH$_2$-thiazol-4-yl | —H | —H | —H | 513.1 | 511.1 | 512.6 |

TABLE 1-continued

| Ex. | R⁵ | R⁷ | R⁸ | R⁹ | R¹⁴ | *ES+ | *ES− | *EI |
|---|---|---|---|---|---|---|---|---|
| 42 | —H | —O—CH₂-(tetrahydro-furan-2-yl) | —CH₃ | —H | —H | 514.1 | 512.1 | 513.6 |
| 43 | —H | —O—(CH₂)₂-cyclohexyl | —H | —H | —H | 526.1 | 524.2 | |
| 44 | —H | —N(CH₃)₂ | —OCH₃ | —H | —F | 545 | | |
| 45 | —H | —OCH₃ | —SCH₃ | —H | —H | 476.1 | 474.1 | 475.6 |
| 46 | —H | —H | —OCH₃ | —OCH₃ | —F | 532 | | |
| 47 | —H | —H | —OCH₃ | —O—(CH₂)₂—OCH₃ | —F | 576 | | |
| 48 | —H | —CH₃ | —H | —H | —H | 414.1 | | |
| 49 | —H | —H | —CH₃ | —H | —H | 414.1 | | |
| 50 | —H | —O—CH₂CH₃ | —H | —H | —H | 444.0 | | |
| 51 | —H | —H | —H | —C(O)—CH₃ | —H | 442.0 | | |
| 52 | —F | —N(CH₃)₂ | —OCH₃ | —H | —H | 491 | | |
| 53 | —F | —H | —CH=N—N(CH₃)— | | —H | 458 | | |
| 54 | —H | —OCH₃ | —OCH₃ | —H | —F | 562 | | |
| 55 | H | —NHCH₃ | H | H | H | 429 | | |
| 56 | H | —CH₃ | —NHCH₃ | H | H | 443 | | |
| 57 | H | —NH—(CH₂)₂—OCH₃ | —CH₃ | H | H | 487 | | |
| 58 | H | —NHCH₃ | —CH₂—CH₃ | H | H | | | |
| 59 | H | —NHCH₃ | F | H | H | | | |
| 60 | H | —NHCH₃ | Cl | H | H | | | |
| 61 | H | —NHCH₃ | Br | H | H | | | |
| 62 | H | —CF₃ | NH₂ | H | H | | | |
| 63 | H | —CF₃ | —NHCH₃ | H | H | | | |
| 64 | H | —COOH | —NH₂ | H | H | | | |
| 65 | H | —NHCH₂CH₃ | —CH₃ | H | H | | | |
| 66 | H | —NHCH₂CH₃ | —CH₃ | H | H | | | |
| 67 | H | —NHCH₂CH₂CH₂OCH₃ | —CH₃ | H | H | | | |
| 68 | H | —CH₃ | —NH—CH₂CH₃ | H | H | | | |
| 69 | H | —CH₃ | —NH—CH₂CH₂CH₃ | H | H | | | |

The compounds of formula X₂

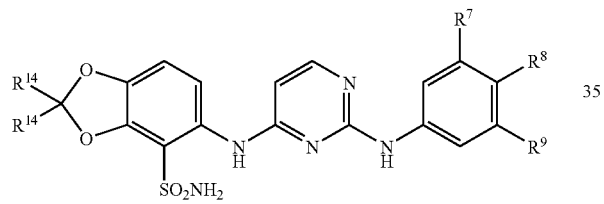

wherein R⁷, R⁸, R⁹ and R¹⁴ are as defined in Table 2, may be prepared by following one of the above procedures but using the appropriate starting materials.

TABLE 2

| Ex. | R⁷ | R⁸ | R⁹ | R¹⁴ | *ES+ | *ES− | *EI |
|---|---|---|---|---|---|---|---|
| 70 | —N(CH₃)₂ | —OCH₃ | —H | —F | 495 | | |
| 71 | —H | —OCH₃ | —OCH₃ | —F | 482 | | |
| 72 | —H | —OCH₃ | —O—(CH₂)₂—OCH₃ | —F | 526 | | |
| 73 | —N(CH₃)₂ | —OCH₃ | —H | —H | 459 | | |
| 74 | —H | —CH=N—N(CH₃)— | | —H | 440 | | |
| 75 | —H | —OCH₃ | —O—(CH₂)₂—OCH₃ | —H | 490 | | |
| 76 | —OCH₃ | —OCH₃ | —OCH₃ | —F | 512 | | |

The compounds of formula $X_3$

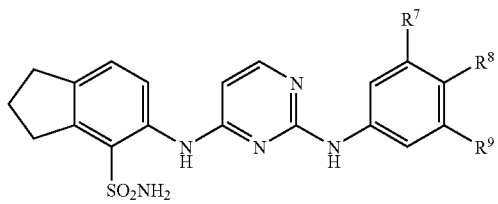

wherein $R^7$, $R^8$ and $R^9$ are as defined in Table 3, may be prepared by following one of the above procedures but using the appropriate starting materials.

The compounds of formula $X_5$

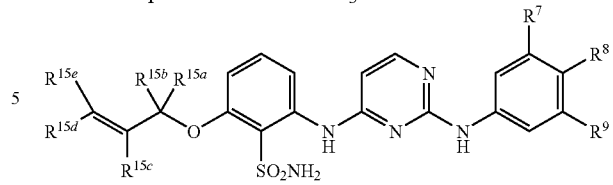

wherein $R^7$, $R^8$, $R^9$ and $R^{15a-e}$ are as defined in Table 4, may be prepared by following one of the above procedures but using the appropriate starting materials.

TABLE 4

| | | | | | | | | MS Data | |
|---|---|---|---|---|---|---|---|---|---|
| Ex. | $R^7$ | $R^8$ | $R^9$ | $R^{15a}$ | $R^{15b}$ | $R^{15c}$ | $R^{15d}$ | $R^{15e}$ | *ES+ | *ES− |
| 87 | —H | —CH=N—N(CH$_3$)— | —H | —H | —H | —H | —H | | 452 | 450 |
| 88 | —N(CH$_3$)$_2$ | —OCH$_3$ | —H | —H | —H | —H | —H | —H | 471 | 469 |
| 89 | —OCH$_3$ | —OCH$_3$ | —H | —H | —H | —Cl | —H | —H | | 490 |
| 90 | —H | —CH=N—N(CH$_3$)— | —H | —H | —H | —Cl | —H | —H | | 484 |
| 91 | —N(CH$_3$)$_2$ | —OCH$_3$ | —H | —H | —H | —Cl | —H | —H | | 505/503 |
| 92 | —OCH$_3$ | —OCH$_3$ | —H | —F | —F | —F | —H | —H | 512 | |
| 93 | —OCH$_3$ | —OCH$_3$ | —H | —H | —H | —F | —F | —F | 512 | 510 |
| 94 | —N(CH$_3$)$_2$ | —OCH$_3$ | —H | —H | —H | —F | —F | —F | 525 | 523 |
| 95 | —H | —CH=N—N(CH$_3$)— | —H | —H | —H | —F | —F | —F | 505 | 503 |
| 96 | —OCH$_3$ | —OCH$_3$ | —H | —H | —H | —F | —H | —H | 476 | 474 |
| 97 | —H | —CH=N—N(CH$_3$)— | —H | —H | —H | —F | —H | —H | 470 | 468 |
| 98 | —N(CH$_3$)$_2$ | —OCH$_3$ | —H | —H | —H | —F | —H | —H | 489 | 487 |

The compounds of formula $X_6$

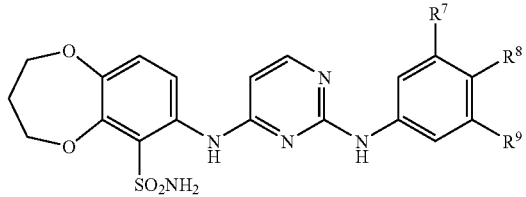

wherein $R^7$, $R^8$, and $R^9$ are as defined in Table 5, may be prepared by following one of the above procedures but using the appropriate starting materials.

TABLE 3

| | | | MS Data | | |
|---|---|---|---|---|---|
| Ex. | $R^7$ | $R^8$ | $R^9$ | *ES+ | *ES− | *EI |
| 77 | —OCH$_3$ | —OCH$_3$ | —H | 442.2 | 440.3 | |
| 78 | —H | —CH=N—NH— | | 422.2 | 420.2 | |
| 79 | —O—(CH$_2$)$_2$-(4-methyl-piperazin-1-yl) | —H | —H | 524.2 | 522.3 | |
| 80 | —O—(CH$_2$)$_2$-piperidino | —H | —H | 509.3 | 507.3 | |
| 81 | —O—(CH$_2$)$_2$-morpholino | —H | —H | 511.2 | 509.3 | |
| 82 | —N(CH$_3$)$_2$ | —OCH$_3$ | —H | 455.2 | 453.3 | |
| 83 | —O—(CH$_2$)$_2$-piperidino | —OCH$_3$ | —H | 539.2 | 537.3 | |
| 84 | —O—(CH$_2$)$_2$-morpholino | —OCH$_3$ | —H | 541.2 | 539.2 | |
| 85 | —O—(CH$_2$)$_2$—OCH$_3$ | —OCH$_3$ | —H | 486.2 | 484.2 | |

A compound of formula $X_4$ (Example 86)

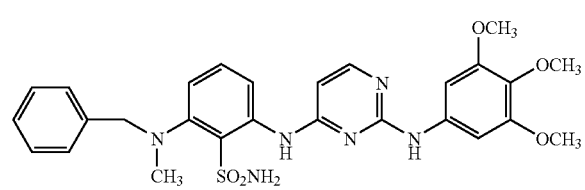

may be prepared by following the procedure of Example 4 but using the appropriate starting materials.

TABLE 5

| | | | | MS Data | | |
|---|---|---|---|---|---|---|
| Ex. | $R^7$ | $R^8$ | $R^9$ | *ES+ | *ES− | *EI |
| 99 | —OCH$_3$ | —OCH$_3$ | —H | 474.1 | 472.2 | |
| 100 | —O—(CH$_2$)$_2$-morpholino | —H | —H | 543.1 | 541.2 | |
| 101 | —N(CH$_3$)$_2$ | —OCH$_3$ | —H | 487.1 | 485.2 | |
| 102 | —O—(CH$_2$)$_2$-piperidino | —H | —H | 541.2 | 539.2 | |
| 103 | —O—(CH$_2$)$_2$-(4-methyl-piperazin-1-yl) | —H | —H | 556.2 | 554.2 | |

EXAMPLE 104

2-[2-(4-Methyl-3-methylamino-phenylamino)-pyrimidine-4-ylamino]-6-(2,2,2-trifluoro-ethoxy)-benzenesulfonamide

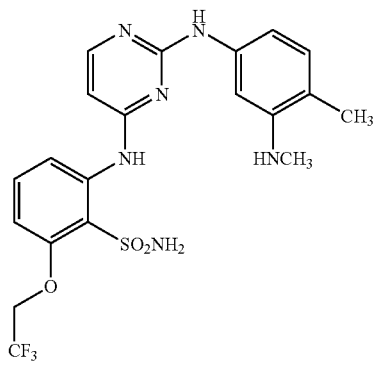

a) $N^3$-benzyl-$N^1$-(4-chloro-pyrimidin-2-yl)-4,$N^3$-dimethyl-benzene-1,3-diamine

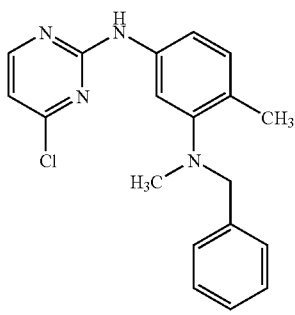

N-benzyl-N,2-dimethyl-5-nitro-aniline: $K_2CO_3$ (270 mg) is added to a solution of N,2-dimethyl-5-nitro-aniline (214.5 mg, 1.29 mmol) and benzyl bromide (0.2 mL, 1.7 mmol) in DMF (4 mL). The mixture is heated for 12 h to 70° C. under stirring. Volatiles are evaporated at reduced pressure. Chromatography of the residue (silica gel, hexane/EtOAc 4:1) yields N-Benzyl-N,2-dimethyl-5-nitro-aniline.

$N^3$-Benzyl-$N^3$,4-dimethyl-benzene-1,3-diamine $SnCl_2$-dihydrate (1117 mg, 4.95 mmol) is added to a solution of N-Benzyl-N,2-dimethyl-5-nitro-aniline (247 mg, 0.96 mmol) in methanol (10 mL) and conc. HCl (1 mL). After boiling under reflux for 2.5 h, volatiles are evaporated under reduced pressure and the residue is partitioned between EtOAc and water, the pH being adjusted to approx. 10 by the addition of 2N NaOH. The organic layer is washed with sat. brine, dried ($Na_2SO_4$), and evaporated. Chromatography of the residue (silica gel, hexanes/EtOAc 3:2) yields $N^3$-benzyl-$N^3$,4-dimethyl-benzene-1,3-diamine.

$N^3$-Benzyl-$N^1$-(4-hydroxy-pyrimidin-2-yl)-$N^3$,4-dimethyl-benzene-1,3-diamine

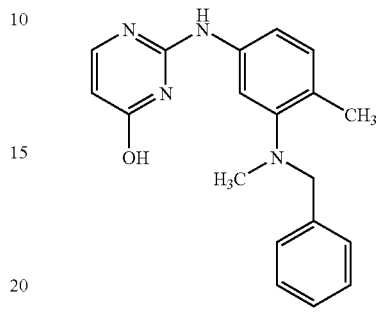

An intimate mixture of $N^3$-benzyl-$N^3$,4-dimethyl-benzene-1,3-diamine (158 mg, 0.7 mmol) and 4-hydroxy-2-methylthio-pyrimidine (109 mg, 0.77 mmol) is heated in an oil bath of 160° C. After 3 h the melt is cooled to room temperature and treated with MeOH. The remaining solid is collected by filtration, washed with MeOH, and dried, giving 65.5 mg (29%) of $N^3$-benzyl-$N^1$-(4-hydroxy-pyrimidin-2-yl)-$N^3$,4-dimethyl-benzene-1,3-diamine.

$N^3$-Benzyl-$N^1$-(4-chloro-pyrimidin-2-yl)-$N^3$,4-dimethyl-benzene-1,3-diamine

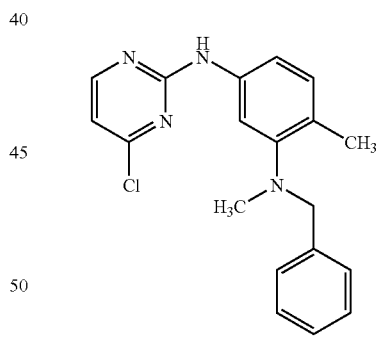

To a solution of $N^3$-benzyl-$N^1$-(4-hydroxy-pyrimidin-2-yl)-$N^3$,4-dimethyl-benzene-1,3-diamine (72 mg, 0.226 mmol) in DMF (2 mL) chloromethylene-N,N-dimethyl-ammonium chloride (Vilsmeyer reagent, 49 mg, 2.384 mmol) is added under argon. After stirring for 20 min at 70° C. another 50 mg (0.39 mmol) of Vilsmeyer reagent is added, and stirring at 70° C. is continued for 13 h. The mixture is partitioned between EtAc and 10 proz. $NaHCO_3$ solution. Chromatography of the residue of the organic phase (silica gel, $CH_2Cl_2$/EtOAc 95:5 gives $N^3$-benzyl-$N^1$-(4-chloro-pyrimidin-2-yl)-$N^3$,4-dimethyl-benzene-1,3-diamine. $^1$H-NMR (400 MHz, DMSO-$d_6$): 2.30 (s, $CH_3$—C(4)); 2.41 (s, $NCH_3$); 3.92 (s, $NCH_2C_6H_5$); 6.78 (dd, J=8 and 2, H—C(6)); 6.92 (d, J=2, H—C(2)); 7.14-7.23 and 7.23-7.35 (2m, H—C(5), NCH$_2$C$_6$H$_5$); 7.40 (d, J=5, H—C(5')); 8.55 (d, J=5, H—C(6')); 9.67 (s, NH).

b) 2-[2-(4-Methyl-3-methylamino-phenylamino)-pyrimidine-4-ylamino]-6-(2,2,2-trifluoro-ethoxy)-benzenesulfonamide

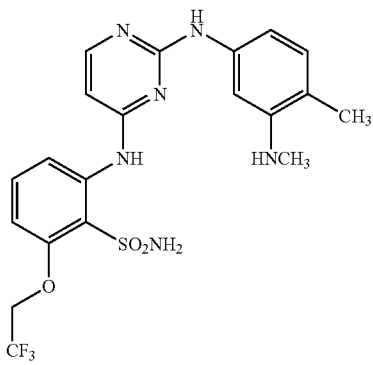

2-Methoxy-6-nitro-benzenesulfonyl chloride

To a mechanically stirred solution of finely pulverized 2-methoxy-6-nitro-aniline (14.7 g, 87.5 mmol) in 80 mL of 37% hydrochloric acid a solution of NaNO$_2$ (7.3 g, 105 mmol) in water (25 mL) is added at −5 to −10° C. within 30 min. Stirring at −10° C. is continued for 30 min, before the mixture is poured into a solution of CuCl (2 g) and CuCl$_2$ (2 g) in AcOH (100 mL) and water (5 mL) cooled to 10° C., which has been saturated with SO$_2$ by bubbling SO$_2$-gas through the solution for 30 min at room temperature, thereby the temperature rises to 15° C. Introduction of SO$_2$-gas is continued for 1 h at room temperature. The precipitated crystals are collected by filtration, yielding 2-methoxy-6-nitro-benzenesulfonyl chloride.

2-Methoxy-6-nitro-benzenesulfonamide

A mixture of 2-methoxy-6-nitro-benzenesulfonyl chloride (12.8 g, 50.87 mmol) and 25% ammonium hydroxide is swirled at 65° C. on a rotavap. After 15 min the volume of the resulting solution is reduced to half by evaporation of volatiles at reduced pressure. Collecting the precipitate by filtration after cooling gives 2-methoxy-6-nitro-benzenesulfonamide.

N-(1-Dimethylamino-methylidene)-2-nitro-6-methoxy-benzenesulfonamide

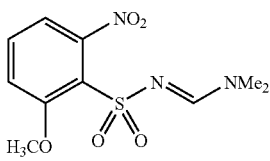

A solution of 2-methoxy-6-nitro-benzenesulfonamide (904 mg, 3.89 mmol) and N,N-dimethyl-formamide dimethyl-acetal (0.78 mL, 5.83 mmol) in DMF (20 mL) is heated for 30 min to 60° C. Evaporation of volatiles at 50° C. under reduced pressure, addition of MeOH to the solid residue, and filtration gives N-[1-dimethylamino-methylidene]-2-nitro-6-methoxy-benzenesulfonamide.

N-(1-Dimethylamino-methylidene)-2-nitro-6-hydroxy-benzenesulfonamide

To a solution of N-[1-dimethylamino-methylidene]-2-nitro-6-methoxy-benzenesulfonamide (956 mg, 3.33 mmol) in dichloromethane (50 mL) BBr$_3$ (0.64 mL, 6.64 mmol is added under stirring at room temperature. After stirring for 30 min the 4 mixture is diluted with CH$_2$Cl$_2$ and extracted twice with saturated brine. Drying of the organic phase with Na$_2$SO$_4$, evaporation of solvent, addition of hexanes to the residue, and filtration gives N-(1-dimethylamino-methylidene)-2-nitro-6-hydroxy-benzenesulfonamide.

N-(1-Dimethylamino-methylidene)-2-nitro-6-(2,2,2-trifluoro-ethoxy)-benzenesulfonamide

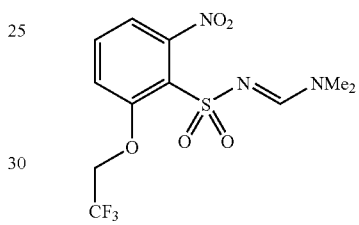

To a solution of N-(1-dimethylamino-methylidene)-2-nitro-6-hydroxy-benzenesulfonamide (847 mg, 3.1 mmol) in DMF (10 mL) NaH (135 mg, 55% dispersion in Nujol, 3.1 mmol) is added under argon. After stirring for 15 min 2,2,2-trifluoro-ethyl iodide (2777 mg, 12.4 mmol) is added, and stirring is continued for 20 h. Volatiles are evaporated under reduced pressure, and the residue is partitioned between EtOAc and water. The organic phase is washed with saturated brine, dried (Na$_2$SO$_4$) and evaporated. Chromatography of the residue (silica gel, hexanes/EtOAc/acetone 2:1:3) gives N-(1-dimethylamino-methylidene)-2-nitro-6-(2,2,2-trifluoro-ethoxy)-benzenesulfonamide.

2-Nitro-6-(2,2,2-trifluoro-ethoxy)-benzenesulfonamide

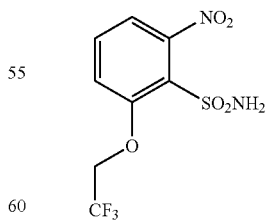

0.2 mL of conc. HCl are added to a suspension of N-(1-dimethylamino-methylidene)-2-nitro-6-(2,2,2-trifluoro-ethoxy)-benzenesulfonamide (262.9 mg, 0.74 mmol) in EtOH (10 mL). After heating to 85° C. for 19 h the mixture is cooled. Filtration affords 130 mg (49%) of starting material.

The filtrate is evaporated, the residue chromatographed on silica gel. Elution with EtOAc/hexanes=2:1 gives 2-Nitro-6-(2,2,2-trifluoro-ethoxy)-benzenesulfonamide:

2-Amino-6-(2,2,2-trifluoro-ethoxy)-benzenesulfonamide

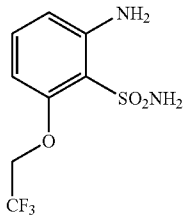

30 mg of 10% Pd on carbon are added to a solution of 2-nitro-6-(2,2,2-trifluoro-ethoxy)-benzenesulfonamide (63 mg, 0.21 mmol) in EtOH (10 mL). The mixture is stirred for 30 min under hydrogen. The catalyst is removed by filtration. Evaporation of solvent gives 2-amino-6-(2,2,2-trifluoro-ethoxy)-benzenesulfonamide.

2-{2-[3-(Benzyl-methyl-amino)-4-methyl-phenylamino]-pyrimidine-4-ylamino}-6-(2,2,2-trifluoro-ethoxy)-benzenesulfonamide

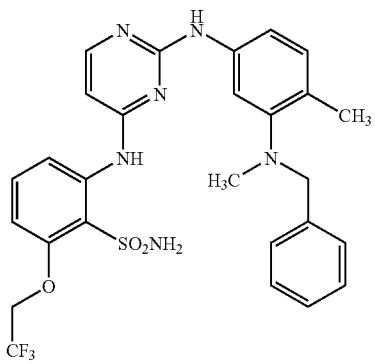

A solution of 2-amino-6-(2,2,2-trifluoro-ethoxy)-benzenesulfonamide (54 mg, 0.2 mmol) and $N^3$-benzyl-$N^1$-(4-chloro-pyrimidin-2-yl)-$N^3$,4-dimethyl-benzene-1,3-diamine (according to step a), 55 mg, 0.163 mmol) in 2-propanol (6 mL) and 1M HCl (0.32 mL) is heated under reflux for 1 h. Solvents are evaporated and the residue is adjusted to pH 8 by the addition of aqueous $NH_3$. Partition between EtOAc and water, washing with 10% brine, drying of the organic phase ($Na_2SO_4$), evaporation of solvents, and chromatography (silica gel) of the residue gives 2-{2-[3-(benzyl-methyl-amino)-4-methyl-phenylamino]-pyrimidine-4-ylamino}-6-(2,2,2-trifluoro-ethoxy)-benzenesulfonamide, eluted with EtOAc/hexanes 2:3. $^1$H-NMR (400 MHz, DMSO-$d_6$): 2.20 (s, $CH_3C(4")$); 2.43 (s, $NCH_3$); 3.90 (s, $NCH_2C_6H_5$); 4.90 (q, J=9, $OCH_2CF_3$); 6.20 (d, J=5, H—C(5')); 6.93 and 6.97 (2d, J=9; H—C(5), H—C(5")); 7.14-7.20, 7.20-7.34, and 7.34-7.4 (3m, $NCH_2C_6H_5$, H—C(2"), H—C(6"), $SO_2NH_2$); 7.45 (t, J=8, H—C(4)); 8.05 (d, J=5, H—C(6')); 8.12 (db, J=9, H—C(3')); 9.12 (b, NH); 8.9-10.3 (NH).

2-[2-(4-Methyl-3-methylamino-phenylamino)-pyrimidine-4-ylamino]-6-(2,2,2-trifluoro-ethoxy)-benzenesulfonamide

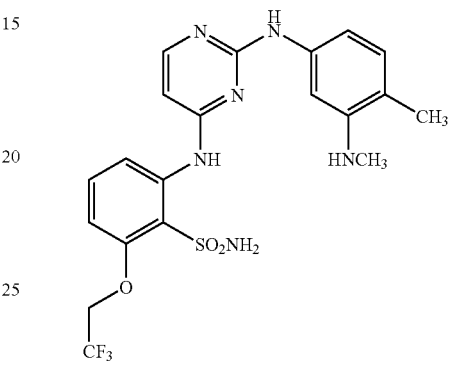

A suspension of 44 mg 20% $Pd(OH)_2$ on charcoal in EtOH (10 mL) is treated with $H_2$ under vigorous stirring. To this 2-{2-[3-(benzyl-methyl-amino)-4-methyl-phenylamino]-pyrimidine-4-ylamino}-6-(2,2,2-trifluoro-ethoxy)-benzenesulfonamide (28 mg, 0.049 mmol) and 0.1 mL of 1M HCl are added (final volume ca. 20 mL). After stirring for 30 min under $H_2$ the catalyst is removed by filtration and the residue of the filtrate, neutralized with ammonia, is purified by chromatography (silica gel, $CH_2Cl_2/CH_3OH$ 95:5), yielding the title compound. $^1$H-NMR (400 MHz, DMSO-$d_6$): 1.95 (s, $CH_3$—C(4")); 2.59 (d, J=5, $NHCH_3$); 4.83 (q, J=5, $NHCH_3$); 4.90 (q, J=9.4, $OCH_2CF_3$); 6.15 (d, J=6, H—C(5')); 6.72 (d, J=2, H—C(2")); 6.75 (d, J=8.5, H—C(5")); 6.9 (dd, J=8.5 and 2, H—C(6")); 6.93 (d, J=8.5, H—C(5)); 6.8-7.5 (b, $SO_2NH_2$); 7.4 (t, J=8.5, H—C(4)); 8.03 (d, J=6, H—C(6')); 8.23 (d, J=8.5, H—C(3)); 8.95 (s, NH); 9.0-10.1 (b, NH).

The compounds of formula $X_7$

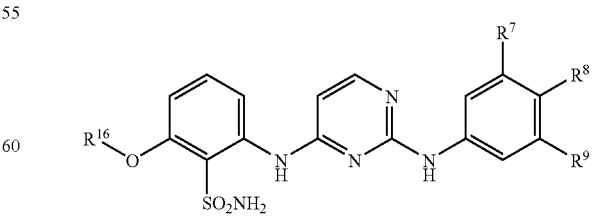

wherein $R^7$, $R^8$, $R^9$ and $R^{16}$ are as defined in Table 6, may be prepared by following one of the above procedures but using the appropriate starting materials.

TABLE 6

| Ex. | $R^{16}$ | $R^7$ | $R^8$ | $R^9$ | MS Data *ES+ | *ES- | *EI |
|---|---|---|---|---|---|---|---|
| 105 | —$CH_2$—$CH_2$—O—$(CH_2)_2$—$OCH_3$ | —$OCH_3$ | —$OCH_3$ | —$OCH_3$ | | | |
| 106 | —$CH_2$—$CH_2$—O—$(CH_2)_2$—$OCH_3$ | —H | —CH=N—$N(CH_3)$— | | | | |
| 107 | —$CH_2$-Ph | —$OCH_3$ | —$OCH_3$ | H | 508 | | |
| 108 | —$CH_2$-Ph | —H | —CH=N—$N(CH_3)$— | | | | |
| 109 | —$(CH_2)_3$—$CF_2$—$CF_3$ | —$OCH_3$ | —$OCH_3$ | H | 578 | | |
| 110 | —$(CH_2)_3$—$CF_2$—$CF_3$ | —$N(CH_3)_2$ | —$OCH_3$ | H | 591 | | |
| 111 | —$(CH_2)_2$—$CH_3$ | —$OCH_3$ | —$OCH_3$ | H | 460 | | |
| 112 | —$CH_2$—$CF_3$ | —$OCH_3$ | —$OCH_3$ | H | 500 | | |
| 113 | —$CH_2$—$CF_3$ | —$N(CH_3)_2$ | —$OCH_3$ | H | 513 | | |
| 114 | —$CHF_2$ | —$OCH_3$ | —$OCH_3$ | H | 468 | | |
| 115 | —$CHF_2$ | —$N(CH_3)_2$ | —$OCH_3$ | H | 481 | | |
| 116 | —$CF_3$ | —O—$(CH_2)_2$—$OCH_3$ | —$OCH_3$ | H | 530 | | |
| 117 | —$CF_3$ | —H | —CH=N—$N(CH_3)$— | | 480 | | |
| 118 | —$CF_3$ | —$N(CH_3)_2$ | —$OCH_3$ | H | 499 | | |
| 119 | —$CH_2$—$CF_3$ | —$NHCH_3$ | —$CH_3$ | H | | | |
| 120 | —$CH_2$—CH=$CH_2$ | —$NHCH_3$ | —$CH_3$ | H | | | |
| 121 | —$CH_2$—C≡CH | —$NHCH_3$ | —$CH_3$ | H | | | |
| 122 | —$CH_2CH_2OCH_3$ | —$NHCH_3$ | —$CH_3$ | H | | | |
| 123 | —$CH_2CH_2$—CN | —$NHCH_3$ | —$CH_3$ | H | | | |
| 124 | —$CH_3$ | —$NHCH_3$ | H | H | 401 | | |
| 125 | —$CH_3$ | $CH_3$ | $NH_2$ | H | 415 | | |
| 126 | —$CH_3$ | $NHCH_2CH_2OCH_3$ | $CH_3$ | H | 459 | | |
| 127 | —$CH_3$ | —$NHCH_3$ | —$CH_2CH_3$ | H | | | |
| 128 | —$CH_3$ | —$NHCH_3$ | F | H | | | |
| 129 | —$CH_3$ | —$NHCH_3$ | Cl | H | | | |
| 130 | —$CH_3$ | —$NHCH_3$ | Br | H | | | |
| 131 | —$CH_3$ | $CF_3$ | $NH_2$ | H | | | |
| 132 | —$CH_3$ | $CF_3$ | —$NHCH_3$ | H | | | |
| 133 | —$CH_3$ | COOH | $NH_2$ | H | | | |
| 134 | —$CH_3$ | $NHCH_2CH_3$ | $CH_3$ | H | | | |
| 135 | —$CH_3$ | $NHCH_2CH_2CH_3$ | $CH_3$ | H | | | |
| 136 | —$CH_3$ | $NHCH_2CH_2CH_2OCH_3$ | $CH_3$ | H | | | |
| 137 | —$CH_3$ | $CH_3$ | $NHCH_2CH_3$ | H | | | |
| 138 | —$CH_3$ | $CH_3$ | —$NHCH_2CH_2CH_3$ | H | | | |

ES+ means electrospray MS positive mode;
ES– means electrospray MS negative mode; and
EL means electron impact MS.

EXAMPLE 139

2-Methoxy-6-[2-(4-methyl-3-methyl-amino-phenylamino)-pyrimidin-4-ylamino]-benzenesulfonamide

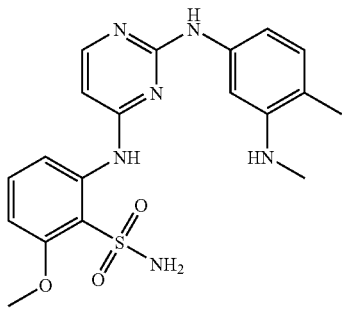

To a suspension of 2.59 g (8.2 mmol) 2-(2-chloro-pyrimidin-4-ylamino)-6-methoxy-benzenesulfonamide and 2.24 g 4,N3-dimethyl-benzene-1,3-diamine in 36 ml isopropanol is added 7.3 ml conc. hydrochloric acid and the reaction mixture is heated to reflux for 2 hours. Then the reaction mixture is partitioned between 1 l ethyl acetate and 1 l water. The aqueous layer is adjusted to slightly basic pH by adding $NaHCO_3$. The organic layer is washed a second time with water, dried with $Na_2SO_4$ and partially evaporated to a volume of 10 ml. 50 ml methanol is added and the product is crystallized to give the title compound.

The compounds used as starting material may be prepared as follows:

a)
N-(3-Methoxy-phenyl)-2,2-dimethyl-propionamide

To an ice cooled solution of 20 g (162 mmol) 3-methoxyphenylamine in 400 ml diethylether is added 24.9 ml (178 mmol) triethylamine and slowly within 30 minutes 23.9 ml (195 mmol) pivaloyl chloride. Due to the exothermic reaction the temperature rises despite cooling to 15° C. The temperature is left rising to room temperature, after 1 hour the reaction mixture is poured on ice and extracted with ethyl acetate, washed 2× with water and 1× with brine, dried with $Na_2SO_4$ and evaporated to give a crude product which is purified by two crystallizations from $CH_2Cl_2$/hexane to yield N-(3-methoxy-phenyl)-2,2-dimethyl-propionamide.

b) 2-(2,2-Dimethyl-propionylamino)-6-methoxybenzenesulfinic acid lithium salt

To a solution of 15 g (72 mmol) compound a) in 300 ml THF is added under argon at −60° C. 112.5 ml (180 mmol) n-BuLi (1.6M in hexane). The reaction mixture is left warming to 0 to +5° C. and stirred for 2 hours. The reaction mixture is cooled again to −60° C. and a solution of 37.1 ml (579 mmol) SO$_2$ in diethyl ether is added. The reaction mixture is left warming to 0 to +5° C. and stirred for 30 minutes. The reaction mixture is filtered to give 2-(2,2-dimethyl-propionylamino)-6-methoxy-benzenesulfinic acid lithium salt as a solid residue. The filtrate also contains the product and is evaporated, the residue is dissolved in ethyl acetate and washed 2× with water, dried with Na$_2$SO$_4$ and evaporated to give further product.

c) N-(3-Methoxy-2-sulfamoyl-phenyl)-2,2-dimethyl-propionamide

To a suspension of 21 g (75 mmol) compound b) in 400 ml water is added at 0-5° C. 31.05 g (378 mmol) sodium acetate and in one portion 21.34 g (189 mmol) hydroxylamine-orthosulfonic acid. The reaction mixture is left stirring at room temperature. Crystals formed in the reaction mixture. After 1 hour the crystals were filtered of to give N-(3-methoxy-2-sulfamoyl-phenyl)-2,2-dimethyl-propionamide. The filtrate is evaporated, dissolved in ethyl acetate and washed 2× with water and 1× with brine, dried with Na$_2$SO$_4$ and evaporated. The residue is purified by chromatography on silica eluting with cyclohexane:ethyl acetate 4:6 to give additional product.

d) 2-Amino-6-methoxy-benzene-sulfonamide

To a solution of 11 g (33 mmol) compound c) in 100 ml 1,2-dimethoxyethane is added 100 ml 6N HCl and stirred at 90° C. for 3.5 hours. The reaction mixture is poured onto ice and extracted with ethyl acetate. The organic layer is washed 2× with water and 1× with brine. 1 N NaOH is added to the aqueous phases to pH=13. This basic aqueous phase is extracted with ethyl acetate, which is washed 2× with water and 1× with brine. The organic layer is dried with Na$_2$SO$_4$ and evaporated to give 2-amino-6-methoxy-benzene-sulfonamide.

e) Methyl-(2-methyl-5-nitro-phenyl)-amine

To 6 g NaH (60% in mineral oil, 145 mmol) in 50 ml dimethoxyethane is added under argon within 10 min 18.4 g (121 mmol) 2-methyl-5-nitro-phenylamine. After 20 minutes 15 ml (242 mmol) methyliodide is added. The temperature rises to 28° C. After stirring for 3 hours at room temperature another portion of 7.5 ml (121 mmol) methyliodide is added. After 24 hours 50 ml of water is slowly added and the reaction mixture is partitioned between 1 l of CH$_2$Cl$_2$ and 1 l of water. The organic layer is dried over Na$_2$SO$_4$ and evaporated. The crude product is purified by chromatography on silica gel eluting with ethyl acetate/cyclohexane 1:3 to give in the order of elution an oily residue containing dimethyl-(2-methyl-5-nitro-phenyl)-amine which is discarded, then the desired methyl-(2-methyl-5-nitro-phenyl)-amine.

f) 4,N3-Dimethyl-benzene-1,3-diamine

To a solution of 3.44 g (21 mmol) compound e) in 60 ml methanol is added 50 mg 10% palladium on charcoal and carefully 1.18 g NaBH$_4$. After 15 minutes the reaction mixture is filtered and the filtrate is partitioned between 500 ml CH$_2$Cl$_2$ and 500 ml water. The organic layer is dried over Na$_2$SO$_4$ and evaporated. The crude product is purified by chromatography on silica gel eluting with ethyl acetate/cyclohexane 1:1 to give 4,N3-dimethyl-benzene-1,3-diamine.

g) 2-(2-Chloro-pyrimidin-4-ylamino)-6-methoxy-benzenesulfonamide

To a solution of 7.57 g (37 mmol) compound d) and 16.73 g (112 mmol) 2,4-dichlorpyrimidine in 80 ml N-methylpyrrolidone is added 43 ml HCl 4M in dioxane. The reaction mixture is stirred for 5.5 hours at 60° C. The reaction mixture is partitioned between 1.5 l ethyl acetate and 1 l water. The aqueous layer is adjusted to slightly basic pH by adding NaHCO3. The organic layer is washed a second time with water, dried with Na2SO4 and evaporated. The crude product is purified by chromatography on silica gel eluting with ethyl acetate. During evaporation of the product containing fractions the product started crystallizing. The crystals are filtered off to give 2-(2-chloro-pyrimidin-4-ylamino)-6-methoxy-benzenesulfonamide.

EXAMPLE 140

6-[2-(4-Methyl-3-methylamino-phenylamino)-pyrimidin-4-ylamino]-2,3-dihydro-benzo[1,4]dioxine-5-sulfonic acid amide

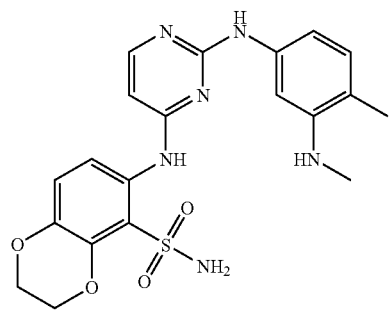

To a suspension of 2.9 g (7.2 mmol) 6-(2-chloro-pyrimidin-4-ylamino)-2,3-dihydro-benzo[1,4]dioxine-5-sulfonic acid amide and 2.0 g 4,N3-dimethyl-benzene-1,3-diamine (compound of Example 102f)) in 50 ml isopropanol is added 5 ml conc. HCl and the reaction mixture is heated to reflux for 2 hours. Then the reaction mixture is partitioned between 1 l ethyl acetate and 1 l water. The aqueous layer is adjusted to slightly basic pH by adding NaHCO$_3$. The water layer is extracted a second time with 300 ml ethyl acetate, the combined organic phases are dried with Na$_2$SO$_4$ and evaporated. The crude product is purified by chromatography on silica gel eluting with ethyl acetate to give in the order of elution a mixture of the two starting materials and the title compound. The mixture of starting materials is again subjected to the reaction conditions and workup giving another 1.21 g (37% yield) of desired product.

6-(2-Chloro-pyrimidin-4-ylamino)-2,3-dihydro-benzo[1,4]dioxine-5-sulfonic acid amide used as starting material may be prepared as follows:

a) N-(2,3-Dihydro-benzo[1,4]dioxin-6-yl)-2,2-dimethyl-propionamide

To a solution of 22.5 g (149 mmol) 2,3-dihydro-benzo[1,4]dioxin-6-ylamine and 25 ml (179 mmol) triethylamine in 1 l diethyl ether is added at 12° C. within 10 minutes 20 ml (164 mmol) pivaloyl chloride dissolved in 250 ml diethyl ether. The temperature is kept between 12-16° C. The reaction mixture is stirred at room temperature for 1 hour. Then it is washed with 2× with 300 ml water, 2× with 150 ml 1N HCl and 2× with brine, dried with Na$_2$SO$_4$ and partially evaporated to a volume of 80 ml. This leads to a suspension. Hexane is added and the solid is filtered to give N-(2,3-Dihydro-benzo[1,4]dioxin-6-yl)-2,2-dimethyl-propionamide.

b) 6-(2,2-Dimethyl-propionyl-amino)-2,3-dihydro-benzo[1,4]dioxine-5-sulfinic acid lithium salt To a solution of 21.45 g (91 mmol) compound a) in 400 ml THF is added under argon at −50° C. 143 ml (228 mmol) n-BuLi (1.6M in hexane). The temperature rises to −5° C. and the reaction mixture is then stirred for 3 hours at 0 to 3° C. 36 g (562 mmol) of $SO_2$ from a pressure bottle is dissolved in ether at −30° C. and this solution is added to the above reaction mixture at −50° C. The reaction mixture is left warming to room temperature. Then 1.3 l of diethyl ether is added and the mixture is filtered. The solid residue is dried to give 24.2 g of 6-(2,2-Dimethyl-propionyl-amino)-2,3-dihydro-benzo[1,4]dioxine-5-sulfinic acid lithium salt.

c) 2,2-Dimethyl-N-(5-sulfamoyl-2,3-dihydro-benzo[1,4]dioxin-6-yl)-propionamide To a solution of 5 g (16 mmol) compound b) in 30 ml water is added at 9° C. 6.7 g (82 mmol) sodium acetate and 4.63 g (41 mmol) hydroxylamine-orthosulfonic acid. The temperature rises to 24° C. despite ice bath cooling. The reaction mixture is extracted with ethyl acetate, the organic phase is washed with water, 10% aqueous $NaHCO_3$ solution, and brine, dried with $Na_2SO_4$ and evaporated to give 2,2-dimethyl-N-(5-sulfamoyl-2,3-dihydro-benzo[1,4]dioxin-6-yl)-propionamide.

d) 6-Amino-2,3-dihydro-benzo[1,4]dioxine-5-sulfonic acid amide

To a solution of 7.09 g (22.5 mmol) compound c) in 70 ml 1,2-dimethoxyethane is added 70 ml 6N HCl and stirred at 90° C. for 2 hours. The reaction mixture is partitioned between 600 ml of $CH_2Cl_2$ and 500 ml of water. The aqueous layer is adjusted to slightly basic pH by adding $NaHCO_3$. The organic layer is dried over $Na_2SO_4$ and evaporated. The residue is shown to be starting material. The aqueous layers are extracted more intensively with 2×500 ml ethyl acetate. The organic layer is dried with $Na_2SO_4$ evaporated and crystallized from ethyl acetate to give 6-amino-2,3-dihydro-benzo[1,4]dioxine-5-sulfonic acid amide. Through repeated crystallisations combined with chromatography on Sephadex LH-20 using methanol as eluent additional desired product is isolated.

e) 6-(2-Chloro-pyrimidin-4-ylamino)-2,3-dihydro-benzo[1,4]dioxine-5-sulfonic acid amide To a solution of 5.98 g (26 mmol) compound d) and 15.5 g (103 mmol) 2,4-dichlorpyrimidine in 120 ml isopropanol is added 12 ml conc. HCl. The reaction mixture is stirred for 2.25 hours at 60° C. The reaction mixture is partitioned between 1 l ethyl acetate and 1 l water. The aqueous layer is adjusted to slightly basic pH by adding $NaHCO_3$. The organic layer is dried with $Na_2SO_4$ and partially evaporated to 150 ml and crystallized to give 6-(2-chloro-pyrimidin-4-ylamino)-2,3-dihydro-benzo[1,4]dioxine-5-sulfonic acid amide.

By following the procedure as indicated above, the compounds of Table 7 may be prepared.

TABLE 7

| Example | Structure | IUPAC name | M + H⁺ |
| --- | --- | --- | --- |
| 141 | 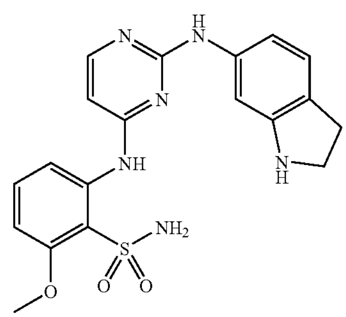 | 2-[2-(2,3-Dihydro-1H-indol-6-ylamino)-pyrimidin-4-ylamino]-6-methoxy-benzenesulfonamide | 413 |
| 142 | 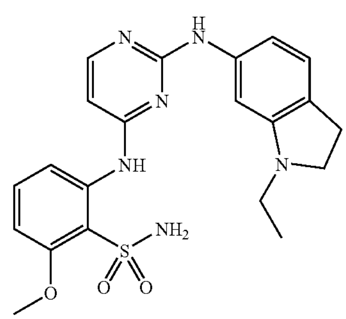 | 2-[2-(1-Ethyl-2,3-dihydro-1H-indol-6-ylamino)-pyrimidin-4-ylamino]-6-methoxy-benzenesulfonamide | 441 |

TABLE 7-continued

| Example | Structure | IUPAC name | M + H⁺ |
|---|---|---|---|
| 143 | 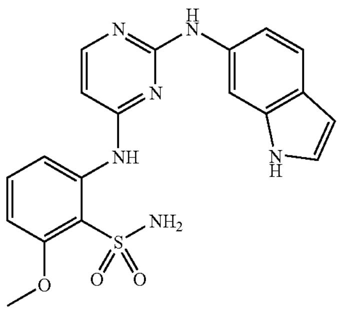 | 2-[2-(1H-Indol-6-ylamino)-pyrimidin-4-ylamino]-6-methoxy-benzenesulfonamide | 411 |
| 144 | 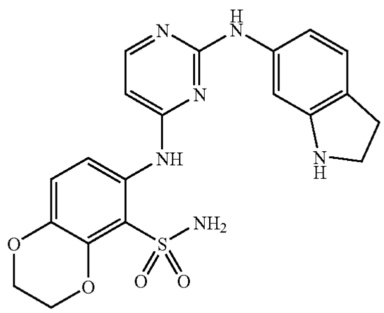 | 6-[2-(2,3-Dihydro-1H-indol-6-ylamino)-pyrimidin-4-ylamino]-2,3-dihydro-benzo[1,4]dioxine-5-sulfonic acid amide | 441 |
| 145 | 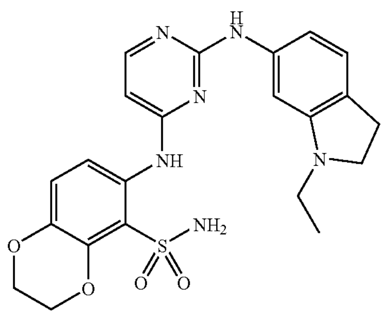 | 6-[2-(1-Ethyl-2,3-dihydro-1H-indol-6-ylamino)-pyrimidin-4-ylamino]-2,3-dihydrobenzo[1,4]dioxine-5-sulfonic acid amide | 469 |
| 146 | 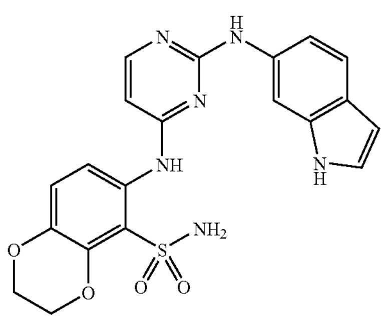 | 6-[2-(1H-Indol-6-ylamino)-pyrimidin-4-ylamino]-2,3-dihydro-benzo[1,4]dioxine-5-sulfonic acid amide | 439 |
| 147 | 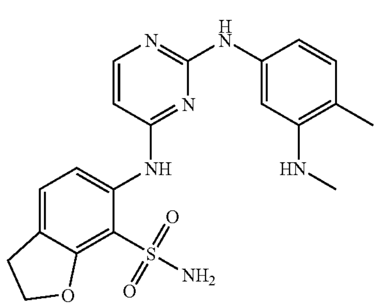 | 6-[2-(4-Methyl-3-methylamino-phenylamino)-pyrimidin-4-ylamino]-2,3-dihydro-benzofuran-7-sulfonic acid amide | |

TABLE 7-continued

| Example | Structure | IUPAC name | M + H⁺ |
|---|---|---|---|
| 148 | 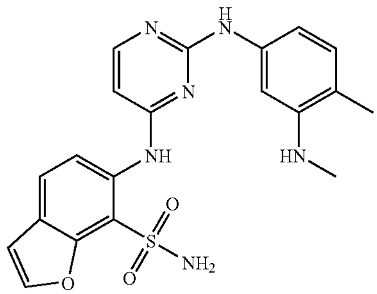 | 6-[2-(4-Methyl-3-methylamino-phenylamino)-pyrimidin-4-ylamino]-benzofuran-7-sulfonic acid amide | |
| 149 | 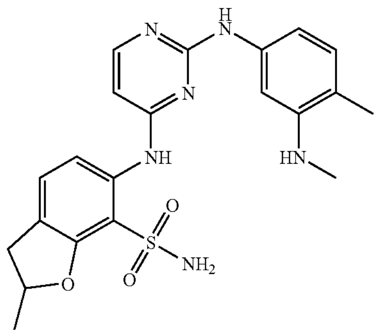 | 2-Methyl-6-[2-(4-methyl-3-methylamino-phenylamino)-pyrimidin-4-ylamino]-2,3-dihydro-benzofuran-7-sulfonic acid amide | |
| 150 | 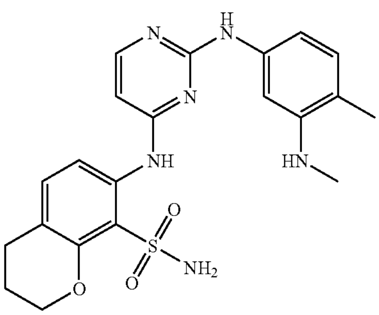 | 7-[2-(4-Methyl-3-methylamino-phenylamino)-pyrimidin-4-ylamino]-chroman-8-sulfonic acid amide | |

The compounds of formula I and their pharmaceutically acceptable salts, exhibit valuable pharmacological properties when tested in in vitro assays, and are therefore useful as pharmaceuticals.

In particular the compounds of the invention exhibit ZAP-70 (zeta chain-associated protein of 70 kD) kinase inhibiting activity and inhibiting activity of the tyrosine kinase activity of anaplastic lymphoma kinase (ALK) and the fusion protein resulting from a gene fusion of nucleophosmin (NPM) and ALK (NPM-ALK), e.g. as demonstrated in accordance with the following test methods.

1. ZAP-70 Cell-Free Kinase Assays

ZAP-70 and Lck (lymphoid T-cell protein tyrosine kinase) are commercially available from Upstate Biotechnology, Lake Placid, N.Y.

ZAP-70 Kinase assay: The activities of the compounds of invention are determined in a homogenous ZAP-70 kinase assay based on time-resolved fluorescence resonance energy transfer. Briefly, 80 nM ZAP-70 are incubated with 80 nM Lck and 4 μM ATP in ZAP-70 kinase buffer (20 mM Tris, pH 7.5, 10 μM Na₃VO₄, 1 mM DTT, 1 mM MnCl₂, 0.01% bovine serum albumin, 0.05% Tween 20) for 1 hour at room temperature in a siliconized polypropylene tube. Then, the selective Lck inhibitor PP2 (4-amino-5-(4-chloro-phenyl)-7-(t-butyl)pyrazolo[3,4-d]pyrimidine; Alexis Biochemicals) is added (final concentration 1.2 μM) and incubated for further 10 min. Ten μl of this solution is mixed with the 10 μl biotinylated peptide LAT-11 (linker for activation of T cell prepared as disclosed in Example 1A of WO 02/12275, the contents of which, particularly with reference to Example 1A, is incorporated herein by reference; 1 μM) as substrate and 20 μl of serial dilutions of inhibitors and incubated for 4 hours at room temperature. The kinase reaction is terminated with 10 μl of a 10 mM EDTA solution in detection buffer (20 mM Tris, pH 7.5, 0.01% bovine serum albumin, 0.05% Tween 20). The detection phase is performed by addition of 50 μl europium (Eu)-labelled anti-phosphotyrosine antibody (e.g. Eu-PT66; final concentration 0.125 nM; Advant/Wallac) and 50 μl streptavidin-allophycocyanine (SA-APC; final concentration 40 nM) in detection buffer. After 1 hour incubation at room temperature fluorescence is measured, e.g., on the Victor2 Multilabel Counter (VVallac) at 665 nm. Background values (low control) are obtained in the absence of test samples and ATP and are subtracted from all values. Signals obtained in the absence of test samples are taken as 100% (high control). The inhibition obtained in the presence of test compounds is calculated as percent inhibition of the high control. The concentration of test compounds resulting in 50% inhibition (IC$_{50}$) is determined from the dose-response curves. In this assay, the compounds of the invention have IC$_{50}$ values in the range of 10 nM to 2 µM, preferably from 10 nM to 100 nM. Compounds of Example 11, 57, 139, 140, 141 and 144 show an IC$_{50}$ value of 16, 13, 37, 10, 183 and 21 nM, respectively.

2. Syk Kinase Assay

Certain compounds of invention also show Syk inhibiting activity determined in a heterogenous Syk kinase assay based on the dissociation-enhanced lanthanide fluoroimmunoassay (DELFIA) technology. This method utilizes europium chelate-labelled anti-phosphotyrosine antibodies to detect phosphate transfer by Syk to a polymeric glutamic acid-tyrosine (Glu, Tyr) substrate coated onto microtiter plates as described (Braunwalder A F, Yarwood D R, Sills M A, Lipson K E. Measurement of the protein tyrosine kinase activity of c-src using time-resolved fluorometry of europium chelates. Anal. Biochem. 1996; 238(2):159-64). The amount of phosphorylation is then quantified with time-resolved, dissociation-enhanced fluorescence. Briefly, hundred µl of poly (Glu, Tyr) (4:1; 2 µg/ml in phosphate-buffered saline, PBS) are coated to ELISA plates overnight at room temperature. The poly (Glu, Tyr) solution is removed and 250 µl of 1% bovine serum albumin in PBS are added for one hour at room temperature. Plates are then washed three times with 350 µl of washing buffer (25 mM Tris-HCl, pH 7.4 containing 0.03% Tween-20). The kinase reaction is performed for one hour at room temperature by mixing serial dilutions of inhibitors in 30 µl with 30 µl of Syk kinase (20 ng/ml) and ATP (1 µM) in kinase buffer (20 mM Tris, pH 7.5, 10 µM Na$_3$VO$_4$, 1 mM DTT, 10 mM MnCl$_2$, 2 mM MgCl$_2$, 0.01% bovine serum albumin, 0.05% Tween 20). After washing the plates four times as described above 60 µl DELFIA europium N1-labelled anti-phosphotyrosine antibody PY20 (Advant/Wallac) are added (100 ng/ml in 50 mM Tris-HCl, pH7.4, 150 mM NaCl, 20 µM Titriplex V, 0.2% bovine serum albumine, 0.05% Tween-20) and incubated for one hour at room temperature. Plates are washed eight times and 60 µl enhancement solution (Wallac) are added. Fluorescence is determined at 615 nm (Victor2; Wallac). High control values (100% signal) are obtained in absence of test samples and low control values (background) in absence of test samples and ATP. Low controls are subtracted from all values. The inhibition obtained in the presence of test compounds is calculated as percent inhibition of the high control. The concentration of test compounds resulting in 50% inhibition (IC$_{50}$) is determined from the dose-response curves. In this assay, the active compounds of the invention have IC$_{50}$ values in the range of 100 nM to 10 µM.

3. ALK Kinase Assay

The inhibition of ALK tyrosine kinase activity is measured using known methods, for example using the recombinant kinase domain of the ALK in analogy to the VEGF-R kinase assay described in J. Wood et al. Cancer Res. 60, 2178-2189 (2000).

The compounds of the invention potently inhibit the growth of human NPM-ALK overexpressing murine BaF3 cells. The expression of NPM-ALK is achieved by transfecting the BaF3 cell line with an expression vector pClneo™ (Promega Corp., Madison Wis., USA) coding for NPM-ALK and subsequent selection of G418 resistant cells. Non-transfected BaF3 cells depend on IL-3 for cell survival. In contrast NPM-ALK expressing BaF3 cells (named BaF3-NPM-ALK) can proliferate in the absence of IL-3 because they obtain proliferative signal through NPM-ALK kinase. Putative inhibitors of the NPM-ALK kinase therefore abolish the growth signal and result in antiproliferative activity. The antiproliferative activity of putative inhibitors of the NPM-ALK kinase can however be overcome by addition of IL-3 which provides growth signals through an NPM-ALK independent mechanism. [for an analogous cell system using FLT3 kinase see E Weisberg et al. Cancer Cell; 1, 433-443 (2002). The inhibitory activity of the compounds of formula I is determined, briefly, as follows: BaF3-NPM-ALK cells (15 000/microtitre plate well) are transferred to 96-well microtitre plates. The test compounds [dissolved in DMSO] are added in a series of concentrations (dilution series) in such a manner that the final concentration of DMSO is not greater than 1% (v/v). After the addition, the plates are incubated for two days during which the control cultures without test compound are able to undergo two cell-division cycles. The growth of the BaF3-NPM-ALK cells is measured by means of Yopro™ staining (T Idziorek et al. J. Immunol. Methods; 185:249-58 [1995]):25 µl of lysis buffer consisting of 20 mM sodium citrate, pH 4.0, 26.8 mM sodium chloride, 0.4% NP40, 20 mM EDTA and 20 mM was added to each well. Cell lysis was completed within 60 min at room temperature and total amount of Yopro bound to DNA was determined by measurement using the Cytofluor II 96-well reader (PerSeptive Biosystems) with the following settings: Excitation (nm) 485/20 and Emission (nm) 530/25.

IC$_{50}$ values are determined by a computer-aided system using the formula:

$$IC_{50}=[(ABS_{test}-ABS_{start})/(ABS_{control}-ABS_{start})]\times 100.$$

The IC$_{50}$ value in those experiments is given as that concentration of the test compound in question that results in a cell count that is 50% lower than that obtained using the control without inhibitor.

The compounds of the invention exhibit inhibitory activity with an IC$_{50}$ in the range from approximately 0.01 to 1 µM.

2. Allogeneic Mixed Lymphocyte Reaction (MLR)

Compounds of the invention exhibit T cell inhibiting activity. More particular the compounds of the invention prevent T cell activation and/or proliferation in e.g. aqueous solution, e.g. as demonstrated in accordance with the following test method. The two-way MLR is performed according to standard procedures (J. Immunol. Methods, 1973, 2, 279 and Meo T. et al., Immunological Methods, New York, Academic Press, 1979, 227-39). Briefly, spleen cells from CBA and BALB/c mice (1.6×10$^5$ cells from each strain per well in flat bottom tissue culture microtiter plates, 3.2×10$^5$ in total) are incubated in RPMI medium containing 10% FCS, 100 U/ml penicillin, 100 µg/ml streptomycin (Gibco BRL, Basel, Switzerland), 50 µM 2-mercaptoethanol (Fluka, Buchs, Switzerland) and serially diluted compounds. Seven three-fold dilution steps in duplicates per test compound are performed. After four days of incubation 1 µCi $^3$H-thymidine is added. Cells are harvested after an additional five-hour incubation period, and incorporated $^3$H-thymidine is determined according to standard procedures. Background values (low control) of the MLR are the proliferation of BALB/c cells alone. Low controls are subtracted from all values. High controls without any sample are taken as 100% proliferation. Percent inhibition by the samples is calculated, and the concentrations required for 50% inhibition (IC$_{50}$ values) are determined. In this assay, the compounds of the invention have IC$_{50}$ values in the range of 10 nM to 10 µM, preferably from 10 nM to 100 nM. Compound of Example 24 shows an IC$_{50}$ value of 40 nM.

3. In Vivo Transplantation

DA (RT1 n) hearts are heterotopically transplanted into the abdomen of anaesthetized Lewis recipient rats according to standard transplantation procedure. Graft function is monitored by daily palpation of the beating donor heart through the abdominal wall. Rejection is considered to be complete when heart beat stops. Increases of graft survival are obtained in animals treated with a compound of formula I administered orally at a daily dose of 1 to 30 mg/kg bid.

The compounds of the invention are therefore useful in the prevention or treatment of disorders or diseases where ZAP-70 inhibition and/or Syk inhibition play a role, e.g. diseases or disorders mediated by T lymphocytes, B lymphocytes, mast cells and/or eosinophils e.g. acute or chronic rejection of organ or tissue allo- or xenografts, atheriosclerosis, vascular occlusion due to vacular injury such as angioplasty, restenosis, fibrosis (especially pulmonary, but also other types of fibrosis, such as renal fibrosis), angiogenesis, hypertension, heart failure, chronic obstructive pulmonary disease, CNS disease such as Alzheimer disease or amyotrophic lateral sclerosis, cancer, infectious disease such as AIDS, septic shock or adult respiratory distress syndrome, ischemia/reperfusion injury e.g. myocardial infarction, stroke, gut ischemia, renal failure or hermorrhage shock, or traumatic shock. The compounds of the invention are also useful in the treatment and/or prevention of acute or chronic inflammatory diseases or disorders or autoimmune diseases e.g. sarcoidosis, fibroid lung, idiopathic interstitial pneumonia, obstructive airways disease, including conditions such as asthma, intrinsic asthma, extrinsic asthma, dust asthma, particularly chronic or inveterate asthma (for example late asthma and airway hyperreponsiveness), bronchitis, including bronchial asthma, infantile asthma, rheumatoid arthritis, osteoarthritis, systemic lupus erythematosus, nephrotic syndrome lupus, Hashimoto's thyroiditis, multiple sclerosis, myasthenia gravis, type I diabetes mellitus and complications associated therewith, type II adult onset diabetes mellitus, uveitis, nephrotic syndrome, steroid dependent and steroid-resistant nephrosis, palmoplantar pustulosis, allergic encephalomyelitis, glomerulonephritis, psoriasis, psoriatic arthritis, atopic eczema (atopic dermatitis), allergic contact dermatitis, irritant contact dermatitis and further eczematous dermatitises, seborrheic dermatitis, lichen planus, pemphigus, bullous pemphigoid, epidermolysis bullosa, urticaria, angioedemas, vasculitides, erythemas, cutaneous eosinophilias, acne, alopecia greata, eosinophilic fasciitis, atherosclerosis, conjunctivitis, keratoconjunctivitis, keratitis, vernal conjunctivitis, uveitis associated with Behcet's disease, herpetic keratitis, conical cornea, Sjoegren's syndrome, dystorphia epithelialis corneae, keratoleukoma, ocular pemphigus, Mooren's ulcer, scleritis, Graves' opthalmopathy, severe intraocular inflamma-tion, inflammation of mucosa or blood vessels such as leukotriene B4-mediated diseases, gastric ulcers, vascular damage caused by ischemic diseases and thrombosis, ischemic bowel disease, inflammatory bowel disease (e.g. Crohn's disease or ulcerative colitis), necrotizing enterocolitis, renal diseases including interstitial nephritis, Goodpasture's syndrome hemolytic uremic syndrome and diabetic nephropathy, nervous diseases selected from multiple myositis, Guillain-Barre syndrome, Meniere's disease and radiculopathy, collagen disease including scleroderma, Wegener's granuloma and Sjogren' syndrome, chronic autoimmune liver diseases including autoim-mune hepatitis, primary biliary cirrhosis and sclerosing cholangitis), partial liver resection, acute liver necrosis (e.g. necrosis caused by toxins, viral hepatitis, shock or anoxia), cirrhosis, fulminant hepatitis, pustular psoriasis, Behcet's disease, active chronic hepatitis, Evans syndrome, pollinosis, idiopathic hypoparathyroidism, Addison disease, autoimmune atrophic gastritis, lupoid hepatitis, tubulointerstitial nephritis, membranous nephritis, or rheumatic fever. The compounds of formula I are useful for treating tumors, e.g. breast cancer, genitourinary cancer, lung cancer, gastrointestinal cancer, epidermoid cancer, melanoma, ovarian cancer, pancreas cancer, neuroblastoma, head and/or neck cancer or bladder cancer, or in a broader sense renal, brain or gastric cancer; in particular (i) a breast tumor; an epidermoid tumor, such as an epidermoid head and/or neck tumor or a mouth tumor; a lung tumor, for example a small cell or non-small cell lung tumor; a gastrointestinal tumor, for example, a colorectal tumor; or a genitourinary tumor, for example, a prostate tumor (especially a hormone-refractory prostate tumor); or (ii) a proliferative disease that is refractory to the treatment with other chemothe-rapeutics; or (iii) a tumor that is refractory to treatment with other chemotherapeutics due to multidrug resistance. They are also useful for treating tumors of blood and lymphatic system (e.g. Hodgkin's disease, Non-Hodgkin's lymphoma, Burkitt's lymphoma, AIDS-related lymphomas, malignant immunoproliferative diseases, multiple myeloma and malignant plasma cell neoplasms, lymphoid leukemia, acute or chronic myeloid leukemia, acute or chronic lymphocytic leukemia, monocytic leukemia, other leukemias of specified cell type, leukemia of unspecified cell type, other and unspecified malignant neoplasms of lymphoid, haematopoietic and related tissues, for example diffuse large cell lymphoma, T-cell lymphoma or cutaneous T-cell lymphoma). Myeloid cancer includes e.g. acute or chronic myeloid leukaemia.

Where a tumor, a tumor disease, a carcinoma or a cancer are mentioned, also metastasis in the original organ or tissue and/or in any other location are implied alternatively or in addition, whatever the location of the tumor and/or metastasis.

For the above uses the required dosage will of course vary depending on the mode of administration, the particular condition to be treated and the effect desired. In general, satisfactory results are indicated to be obtained systemically at daily dosages of from about 0.02 to 25 mg/kg per body weight. An indicated daily dosage in the larger mammal, e.g. humans, is in the range from about 0.2 mg to about 2 g, conveniently administered, for example, in divided doses up to four times a day or in retard form. Suitable unit dosage forms for oral administration comprise from ca.0.1 to 500 mg active ingredient.

The compounds of the invention may be administered by any conventional route, in particular parenterally, for example in the form of injectable solutions or suspensions, enterally, e.g. orally, for example in the form of tablets or capsules, topically, e.g. in the form of lotions, gels, ointments or creams, or in a nasal or a suppository form. Topical administration is e.g. to the skin. A further form of topical administration is to the eye. Pharmaceutical compositions comprising a compound of the invention in association with at least one pharmaceutical acceptable carrier or diluent may be manufactured in conventional manner by mixing with a pharmaceutically acceptable carrier or diluent.

The compounds of formula I may be administered in free form or in pharmaceutically acceptable salt form, e.g. as indicated above. Such salts may be prepared in conventional manner and exhibit the same order of activity as the free compounds.

In accordance with the foregoing, the present invention also provides:

(1) A compound of formula I or a pharmaceutically acceptable salt thereof, for use as a pharmaceutical;

(2) A compound of formula I or a pharmaceutically acceptable salt thereof, for use as a ZAP-70 or ALK inhibitor, for example for use in any of the particular indications hereinbefore set forth;

(3) A pharmaceutical composition, e.g. for use in any of the indications herein before set forth, comprising a compound of formula I or a pharmaceutically acceptable salt thereof, together with one or more pharmaceutically acceptable diluents or carriers therefor.

(4) A method for the treatment of any of particular indication hereinbefore set forth in a subject in need thereof which comprises administering to the subject an effective amount of a compound of formula I or a pharmaceutically acceptable salt thereof;

(5) The use of a compound of formula I or a pharmaceutically acceptable salt thereof, for the manufacture of a medicament for the treatment or prevention of a disease or condition in which ZAP-70 or ALK activation plays a role or is implicated; e.g. as discussed above.

The compounds of formula I may be administered as the sole active ingredient or in conjunction with, e.g. as an adjuvant to, other drugs e.g. in immunosuppressive or immunomodulating regimens or other anti-inflammatory agents, e.g. for the treatment or prevention of allo- or xenograft acute or chronic rejection or inflammatory or autoimmune disorders, a chemotherapeutic agent or an anti-infective agent, e.g. an anti-viral agent such as e.g. an anti-retroviral agent or an antibiotic. For example, the compounds of formula I may be used in combination with a calcineurin inhibitor, e.g. cyclosporin A, ISA 247 or FK 506; an mTOR inhibitor, e.g. rapamycin, 40-O-(2-hydroxyethyl)-rapamycin, CCI779, ABT578, biolimus-7, biolimus-9, TAFA-93, AP23573, AP23464, or AP23841; an ascomycin having immuno-suppressive properties, e.g. ABT-281, ASM981, etc.; corticosteroids; cathepsin S inhibitors; cyclophosphamide; azathioprine; methotrexate; leflunomide; mizoribine; mycophenolic acid; mycophenolate mofetil; 15-deoxyspergualine or an immunosuppressive homologue, analogue or derivative thereof; a sphingosine-1-phosphate receptor agonist, e.g. FTY720 or an analog thereof, e.g Y-36018; monoclonal antibodies to leukocyte receptors, e.g., MHC, CD2, CD3, CD4, CD7, CD8, CD11a/CD18, CD25, CD27, CD28, CD40, CD45, CD58, CD80, CD86, CD137, ICOS, CD150 (SLAM), OX40, 4-1 BB or to their ligands, e.g. CD154, or antagonists thereof; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists, e.g. natalizumab (ANTEGREN®); or anti-chemokine antibodies or antichemokine receptor antibodies or low molecular weight chemokine receptor antagonists, e.g. anti MCP-1 antibodies.

A compound of formula I may also be used in combination with other antiproliferative agents. Such antiproliferative agents include, but are not limited to:

(i) aromatase inhibitors, e.g. steroids, especially exemestane and formestane and, in particular, non-steroids, especially aminoglutethimide, vorozole, fadrozole, anastrozole and, very especially, letrozole;

(ii) antiestrogens, e.g. tamoxifen, fulvestrant, raloxifene and raloxifene hydrochloride;

(iii) topoisomerase I inhibitors, e.g. topotecan, irinotecan, 9-nitrocamptothecin and the macromolecular camptothecin conjugate PNU-166148 (compound A1 in WO99/17804);

(iv) topoisomerase II inhibitors, e.g. the antracyclines doxorubicin (including liposomal formulation, e.g. CAELYXT™), epirubicin, idarubicin and nemorubicin, the anthraquinones mitoxantrone and losoxantrone, and the podophillotoxines etoposide and teniposide;

(v) microtubule active agents, e.g. the taxanes paclitaxel and docetaxel, the vinca alkaloids, e.g., vinblastine, especially vinblastine sulfate, vincristine especially vincristine sulfate, and vinorelbine, discodermolide and epothilones, such as epothilone B and D;

(vi) alkylating agents, e.g. cyclophosphamide, ifosfamide and melphalan;

(vii) histone deacetylase inhibitors;

(viii) farnesyl transferase inhibitors;

(ix) COX-2 inhibitors, e.g. celecoxib (Celebrex®), rofecoxib (Vioxx®) and lumiracoxib (COX189);

(x) MMP inhibitors;

(xi) mTOR inhibitors;

(xii) antineoplastic antimetabolites, e.g. 5-fluorouracil, tegafur, capecitabine, cladribine, cytarabine, fludarabine phosphate, fluorouridine, gemcitabine, 6-mercaptopurine, hydroxyurea, methotrexate, edatrexate and salts of such compounds, and furthermore ZD 1694 (RALTITREXED™), LY231514 (ALIMTA™), LY264618 (LOMOTREXOL™) and OGT719;

(xiii) platin compounds, e.g. carboplatin, cis-platin and oxaliplatin;

(xiv) compounds decreasing the protein kinase activity and further anti-angiogenic compounds, e.g. (i) compounds which decrease the activity of the Vascular Endothelial Growth Factor (VEGF) (b) the Epidermal Growth Factor (EGF), c-Src, protein kinase C, Platelet-derived Growth Factor (PDGF), Bcr-Abl tyrosine kinase, c-kit, Flt-3 and Insulin-like Growth Factor I Receptor (IGF-IR) and Cyclin-dependent kinases (CDKs); (ii) Imatinib, midostaurin, Iressa™ (ZD1839), CGP 75166, vatalanib, ZD6474, GW2016, CHIR-200131, CEP-7055/CEP-5214, CP-547632 and KRN-633; (iii) thalidomide (THALOMID), celecoxib (Celebrex), SU5416 and ZD6126;

(xv) gonadorelin agonists, e.g. abarelix, goserelin and goserelin acetate;

(xvi) anti-androgens, e.g. bicalutamide (CASODEX™);

(xvii) bengamides;

(xviii) bisphosphonates, e.g. etridonic acid, clodronic acid, tiludronic acid, pamidronic acid, alendronic acid, ibandronic acid, risedronic acid and zoledronic acid;

(xix) antiproliferative antibodies, e.g. trastuzumab (Herceptin™), Trastuzumab-DM1, erlotinib (Tarceva™), bevacizumab (Avastin™), rituximab (Rituxan®), PRO64553 (anti-CD40) and 2C4 Antibody;

(xx) temozolomide (TEMODAL®).

The structure of the active agents identified by code nos., generic or trade names may be taken from the actual edition of the standard compendium "The Merck Index" or from databases, e.g. Patents International (e.g. IMS World Publications).

In accordance with the foregoing the present invention provides in a yet further aspect:

(6) A method as defined above comprising co-administration, e.g. concomitantly or in sequence, of a therapeutically effective amount of a) a compound of formula I or a pharmaceutically acceptable salt thereof, and b) a second drug substance, said second drug substance being for example for use in any of the particular indications hereinbefore set forth.

(7) A combination comprising a therapeutically effective amount of a ZAP-70 or a ALK kinase inhibitor, e.g. a compound of formula I or a pharmaceutically acceptable salt thereof, and a second drug substance, said second drug substance being for example as disclosed above.

Where a ZAP-70 or LAK kinase inhibitor, e.g. a compound of formula I, is administered in conjunction with other immunosuppressive/immunomodulatory, anti-inflammatory or antineoplastic agent, e.g. as disclosed above, dosages of the co-administered drug or agent will of course vary depending on the type of co-drug or agent employed, or the specific drug or agent used, or the condition being treated and so forth.

The invention claimed is:

1. A compound of formula I

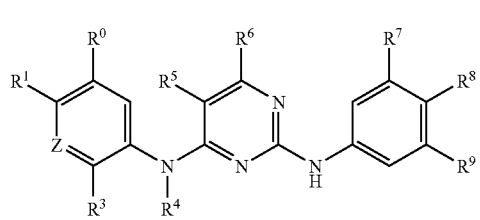

(I)

wherein
Z is =CR$^2$;
R$^0$ is hydrogen;
R$^1$ and R$^2$ form together with the C-atoms to which they are attached a 5 to 15 membered non-aromatic carbocyclyl or heterocyclyl, wherein said heterocyclyl contains 1 to 5 heteroatoms selected from N, O and S;
or R$^1$ is hydrogen; and R$^2$ is C$_{1-4}$-alkoxy;
R$^3$ is —SO$_2$NH$_2$;
R$^4$ and R$^6$ are hydrogen;
R$^5$ is hydrogen; halogen; C$_{1-4}$alkyl; or CF$_3$;
one of R$^7$, R$^8$ and R$^9$ is NR$^{10}$R$^{11}$ and one of the two others is hydrogen, halogen, COOH, CF$_3$ or C$_{1-4}$ alkyl; and the third one is H;
one of R$^{10}$ and R$^{11}$, is hydrogen or C$_{1-4}$alkyl and the other is hydrogen; C$_{1-8}$-alkyl, C$_{1-8}$-alkyl terminally substituted by OH, C$_{3-6}$-cycloalkyl or a heterocyclic ring; C$_{2-8}$alkenyl; C$_{3-8}$-cycloalkyl; C$_{1-8}$alkoxyC$_{1-4}$-alkyl; hydroxyC$_{1-8}$alkoxyC$_{1-8}$alkyl; or a 5 membered heterocyclic ring;
or a salt thereof.

2. The compound of claim 1, wherein
each of R$^0$, R$^4$, R$^5$, R$^6$ and R$^9$ is hydrogen;
R$^3$ is SO$_2$NH$_2$;
R$^1$ is hydrogen and R$^2$ is methoxy;
R$^7$ is NHCH$_3$; and
R$^8$ is CH$_3$
or a salt thereof.

3. The compound according to claim 1 which is
2-Methoxy-6-[2-(4-amino-3-methyl-phenylamino)-pyrimidin-4-ylamino]-benzenesulfonamide;
2-Methoxy-6-[2-(4-ethyl-3-methyl-amino-phenylamino)-pyrimidin-4-ylamino]-benzenesulfonamide;
2-Methoxy-6-[2-(4-methylamino-3-trifluoromethyl-phenylamino)-pyrimidin-4-ylamino]-benzenesulfonamide;
2-methoxy-6-[2-(4-methyl-3-methyl-amino-phenylamino)-pyrimidin-4-ylamino]-benzenesulfonamide;
or a salt thereof.

4. The compound according to claim 3 which is 2-Methoxy-6-[2-(4-amino-3-methyl-phenylamino)-pyrimidin-4-ylamino]-benzenesulfonamide.

5. The compound according to claim 3 which is 2-methoxy-6-[2-(4-methyl-3-methyl-amino-phenylamino)-pyrimidin-4-ylamino]-benzenesulfonamide.

6. A pharmaceutical composition comprising a compound of formula I according to claim 1 or a pharmaceutically acceptable salt thereof, and one or more pharmaceutically acceptable diluents or carriers therefore.

7. A method for treating a disease or a disorder where ZAP-70 inhibition and/or Syk inhibition play a role, comprising: administering to a patient in need thereof, an effective amount of the compound of formula (I) according to claim 1, or a pharmaceutically acceptable salt thereof; wherein said disease or disorder is rheumatoid arthritis.

8. A compound of formula X$_1$

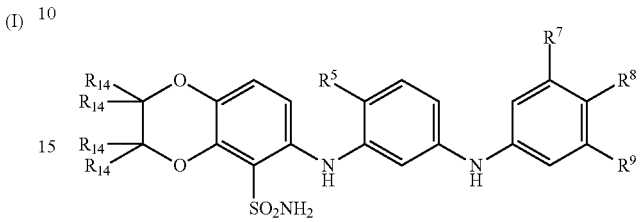

wherein R$^5$, R$^7$, R$^8$, R$^9$ and R$^{14}$ are as defined in Table 1:

TABLE 1

| R$^5$ | R$^7$ | R$^8$ | R$^9$ | R$^{14}$ |
|---|---|---|---|---|
| H | —NHCH$_3$ | H | H | H |
| H | —CH$_3$ | —NHCH$_3$ | H | H |
| H | —NH—(CH$_2$)$_2$—OCH$_3$ | —CH$_3$ | H | H |
| H | —NHCH$_3$ | —CH$_2$—CH$_3$ | H | H |
| H | —NHCH$_3$ | F | H | H |
| H | —NHCH$_3$ | Cl | H | H |
| H | —NHCH$_3$ | Br | H | H |
| H | —CF$_3$ | NH$_2$ | H | H |
| H | —CF$_3$ | —NHCH$_3$ | H | H |
| H | —COOH | —NH$_2$ | H | H |
| H | —NHCH$_2$CH$_3$ | —CH$_3$ | H | H |
| H | NHCH$_2$CH$_2$CH$_3$ | —CH$_3$ | H | H |
| H | —NHCH$_2$CH$_2$CH$_2$OCH$_3$ | —CH$_3$ | H | H |
| H | —CH$_3$ | —NH—CH$_2$CH$_3$ | H | H |
| H | —CH$_3$ | —NH—CH$_2$CH$_2$CH$_3$ | H | H | or a salt thereof.

9. A pharmaceutical composition comprising a compound of formula X$_1$ according to claim 8 or a pharmaceutically acceptable salt thereof, and one or more pharmaceutically acceptable diluents or carriers therefore.

10. A compound of formula X$_7$

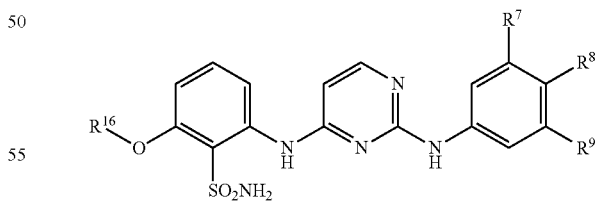

wherein R$^7$, R$^8$, R$^9$ and R$^{16}$ are as defined in Table 6:

TABLE 6

| R$^{16}$ | R$^7$ | R$^8$ | R$^9$ |
|---|---|---|---|
| —CH$_3$ | —NHCH$_3$ | H | H |
| —CH$_3$ | NHCH$_2$CH$_2$OCH$_3$ | CH$_3$ | H |
| —CH$_3$ | —NHCH$_3$ | F | H |

TABLE 6-continued

| $R^{16}$ | $R^7$ | $R^8$ | $R^9$ |
|---|---|---|---|
| —CH$_3$ | —NHCH$_3$ | Cl | H |
| —CH$_3$ | —NHCH$_3$ | Br | H |
| —CH$_3$ | CF$_3$ | NH$_2$ | H |
| —CH$_3$ | COOH | NH$_2$ | H |
| —CH$_3$ | NHCH$_2$CH$_3$ | CH$_3$ | H |
| —CH$_3$ | NHCH$_2$CH$_2$CH$_3$ | CH$_3$ | H |
| —CH$_3$ | NHCH$_2$CH$_2$CH$_2$OCH$_3$ | CH$_3$ | H |
| —CH$_3$ | CH$_3$ | NHCH$_2$CH$_3$ | H |
| —CH$_3$ | CH$_3$ | —NHCH$_2$CH$_3$ | H | or a salt thereof.

11. A pharmaceutical composition comprising a compound of formula X$_7$ according to claim 10 or a pharmaceutically acceptable salt thereof, and one or more pharmaceutically acceptable diluents or carriers therefore.

\* \* \* \* \*